US011179096B2

(12) United States Patent
Kanai et al.

(10) Patent No.: US 11,179,096 B2
(45) Date of Patent: Nov. 23, 2021

(54) SCOLIOSIS DIAGNOSIS ASSISTANCE DEVICE, SCOLIOSIS DIAGNOSIS ASSISTANCE METHOD, AND PROGRAM

(71) Applicants: National University Corporation Hokkaido University, Hokkaido (JP); NOA Co., Ltd., Ibaraki (JP)

(72) Inventors: Satoshi Kanai, Hokkaido (JP); Hideki Sudo, Hokkaido (JP); Yuichiro Abe, Hokkaido (JP); Hiroshi Nagaeda, Hokkaido (JP)

(73) Assignees: NATIONAL UNIVERSITY CORPORATION HOKKAIDO UNIVERSITY, Hokkaido (JP); NOA CO., LTD., Ibaraki (JP)

( * ) Notice: Subject to any disclaimer, the term of this patent is extended or adjusted under 35 U.S.C. 154(b) by 287 days.

(21) Appl. No.: 16/090,946

(22) PCT Filed: Apr. 4, 2017

(86) PCT No.: PCT/JP2017/014082
§ 371 (c)(1),
(2) Date: Oct. 3, 2018

(87) PCT Pub. No.: WO2017/175761
PCT Pub. Date: Oct. 12, 2017

(65) Prior Publication Data
US 2019/0117148 A1 Apr. 25, 2019

(30) Foreign Application Priority Data
Apr. 5, 2016 (JP) .............................. JP2016-075547

(51) Int. Cl.
*A61B 5/00* (2006.01)
*A61B 5/107* (2006.01)
*A61B 6/00* (2006.01)

(52) U.S. Cl.
CPC .......... *A61B 5/4561* (2013.01); *A61B 5/1079* (2013.01); *A61B 6/505* (2013.01);
(Continued)

(58) Field of Classification Search
CPC ..... A61B 5/4561; A61B 5/1079; A61B 6/505; A61B 5/4566; A61B 5/7282; A61B 5/743;
(Continued)

(56) References Cited

U.S. PATENT DOCUMENTS

| 5,080,109 A | 1/1992 | Arme, Jr. |
| 2007/0106182 A1 | 5/2007 | Arnett |

(Continued)

FOREIGN PATENT DOCUMENTS

| JP | 2007-257324 A | 10/2007 |
| JP | 2007257324 A | * 10/2007 |

(Continued)

OTHER PUBLICATIONS

Google Patents translation of JP2007257324A (Year: 2007).*
(Continued)

*Primary Examiner* — Devin B Henson
*Assistant Examiner* — Justin Xu
(74) *Attorney, Agent, or Firm* — Wilmer Cutler Pickering Hale and Dorr LLP

(57) ABSTRACT

A scoliosis diagnosis assistance device includes: a first shape information acquisition module configured to acquire back shape information representing the three-dimensional shape of a back of a subject; a second shape information acquisition module configured to acquire minor-symmetry information representing a three-dimensional shape having a minor-symmetry relationship with the three-dimensional shape of the back of the subject with respect to a sagittal plane of the three-dimensional shape; a deviation distribu- (Continued)

tion acquisition module configured to acquire a distribution of deviation between the three-dimensional shape represented by the back shape information and the three-dimensional shape represented by the mirror-symmetry information; and an output controller configured to cause a display to display the distribution of deviation, for example.

14 Claims, 25 Drawing Sheets

(52) U.S. Cl.
CPC .......... *A61B 5/4566* (2013.01); *A61B 5/7282* (2013.01); *A61B 5/743* (2013.01); *A61B 6/488* (2013.01)

(58) Field of Classification Search
CPC ... A61B 6/488; A61B 5/1116; A61H 2230/62; A63B 2208/02; A63B 2230/62; A63B 2230/625; A63B 23/0244
See application file for complete search history.

(56) References Cited

U.S. PATENT DOCUMENTS

| | | | |
|---|---|---|---|
| 2011/0301500 A1* | 12/2011 | Maguire | A61B 34/30 600/583 |
| 2014/0303522 A1 | 10/2014 | Akimoto et al. | |
| 2015/0223730 A1* | 8/2015 | Ferrantelli | A61B 5/4561 600/476 |
| 2017/0273614 A1* | 9/2017 | Giphart | A61B 6/4014 |

FOREIGN PATENT DOCUMENTS

| | | | |
|---|---|---|---|
| JP | 2014508340 A | * | 1/2012 |
| JP | 2013-165862 A | | 8/2013 |
| JP | 2013-248089 A | | 12/2013 |
| JP | 2014-508340 A | | 4/2014 |
| WO | WO-2012/093353 A1 | | 7/2012 |
| WO | WO-2013/081030 A1 | | 6/2013 |

OTHER PUBLICATIONS

Google Patents translation of JP2014508340A (Year: 2014).*
International Search Report corresponding to PCT/JP2017/014082 dated Jun. 27, 2017 (one page).
Hyoungseop Kim et al., "Spinal Deformity Detection from Moire Images Based on Differences in Gray Values on the Left and Right Sides", Medical Imaging Technology, vol. 21, No. 2, Mar. 2003, pp. 131 to 138.
Japanese Notice of Reasons for Refusal issued in Japanese Patent Application No. 2017-164844, dated Sep. 16, 2020, 8 pages.

* cited by examiner (a)
(b)
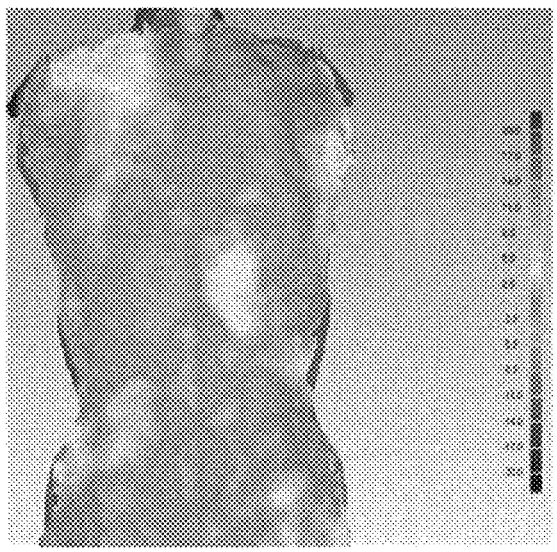
(c)
(d)
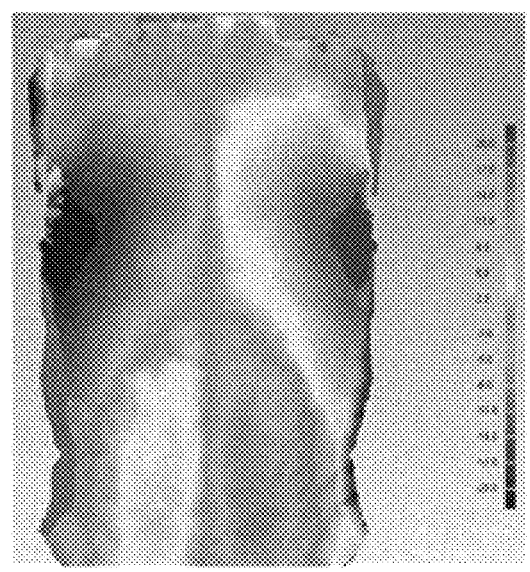
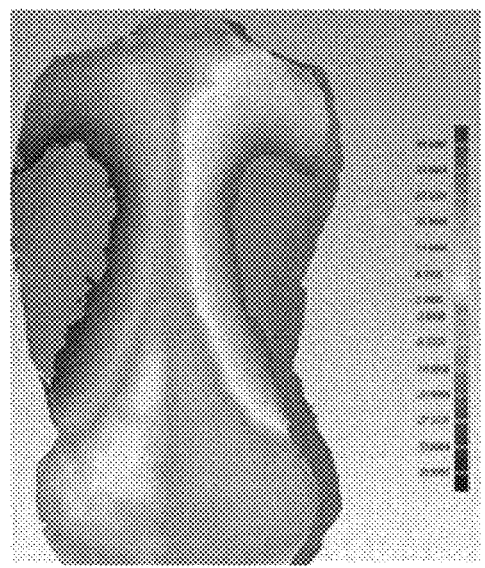
FIG. 11

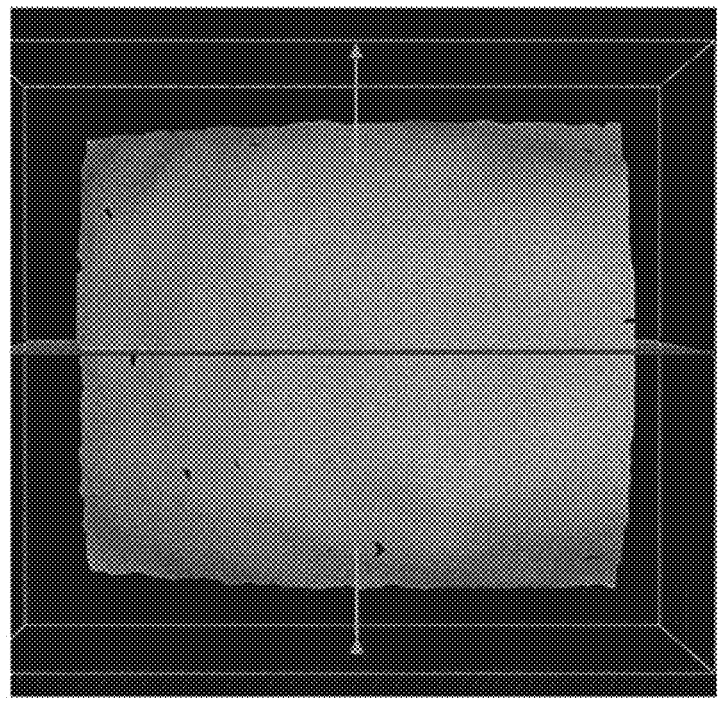
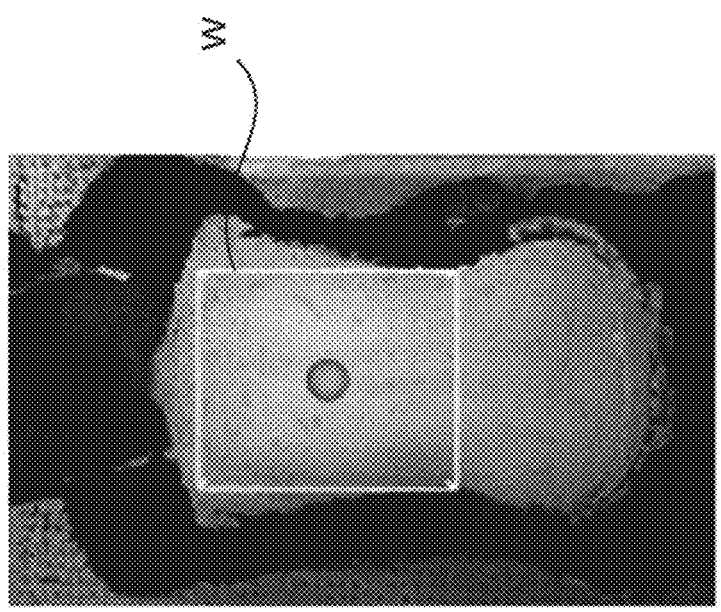
FIG. 19

| SCOLIOSIS TO BE DIAGNOSED | INDEX TYPE | | |
|---|---|---|---|
| Cobb ANGLE OF 25 DEGREES OR MORE | 1ST ASYMMETRIC INDEX | POSITIVE LIKELIHOOD RATIO | 7.29 |
| | | NEGATIVE LIKELIHOOD RATIO | 0.085 |
| Cobb ANGLE OF 25 DEGREES OR MORE | 2ND ASYMMETRIC INDEX | POSITIVE LIKELIHOOD RATIO | 17.75 |
| | | NEGATIVE LIKELIHOOD RATIO | 0.16 |
| Cobb ANGLE OF 15 DEGREES OR MORE | 1ST ASYMMETRIC INDEX | POSITIVE LIKELIHOOD RATIO | 6.88 |
| | | NEGATIVE LIKELIHOOD RATIO | 0.075 |
| Cobb ANGLE OF 15 DEGREES OR MORE | 2ND ASYMMETRIC INDEX | POSITIVE LIKELIHOOD RATIO | 5.88 |
| | | NEGATIVE LIKELIHOOD RATIO | 0.077 |

FIG. 26

SCOLIOSIS DIAGNOSIS ASSISTANCE DEVICE, SCOLIOSIS DIAGNOSIS ASSISTANCE METHOD, AND PROGRAM

CROSS-REFERENCE TO RELATED APPLICATION

This application is a national stage application of International Application No. PCT/JP2017/014082 entitled "Scoliosis Diagnosis Assistance Device, Scoliosis Diagnosis Assistance Method, and Program" filed on Apr. 4, 2017, which claims priority to Japanese Patent Application No. 2016-075547 filed on Apr. 5, 2016, the disclosures of which are hereby incorporated by reference in their entirety.

TECHNICAL FIELD

This invention relates to a scoliosis diagnosis assistance device, a scoliosis diagnosis assistance method, and a program.

BACKGROUND ART

Scoliosis is a disease that causes deformation of a spinal column. A surgery is required when the disease has progressed, whereas the progress may be stopped when the disease is detected in an early stage and treatment is given. Thus, it is extremely important to detect the disease in an early stage.

Scoliosis often occurs in school-age children, and thus a medical examination thereof is mandated by the School Health and Safety Act in Japan. However, the back of a subject is locally twisted as a sign of scoliosis in many cases, resulting in a failure to detect the sign in the medical examination. Against this background, various kinds of systems and other measures for assisting in diagnosis of scoliosis are proposed.

For example, a moire method of measuring the shape of the back of the subject by using interference fringes of light is proposed, but this method usually requires, for example, a large-scale apparatus.

Further, for example, there is known a method of performing a diagnosis by using an X-ray image or a computed tomography (CT) image. Although this method is useful for a definitive diagnosis, in general, there is also a demand for avoiding radiation exposure as much as possible. Besides, a CT scanner for obtaining a CT image is a large-scale apparatus.

In order to be widely adopted in a medical examination, a non-invasive system that does not use, for example, radiation, with a simpler configuration than that of a system adopting the moire method, is desired. For example, systems described in Patent Documents 1 and 2 are proposed as such a system.

For example, a scoliosis screening system described in Patent Document 1 horizontally corrects and binarizes an image obtained by photographing the back of the subject, and then analyzes the image to obtain a predetermined parameter. As the predetermined parameter, in Patent Document 1, the inclination angle of a midline D, the magnitude of a difference between a central value continuous line C and the midline D, the inclination of a shoulder line E, the angle of a waist line G, and a difference between left and right areas of the back of the subject with the midline D serving as its boundary. The central value continuous line C is a line obtained by connecting central values of a shoulder contour line and a waist contour line.

An evaluation system for scoliosis described in Patent Document 2 calculates a difference in height between left and right peak positions of the back of the subject with the midline serving as its boundary based on three-dimensional data obtained by photographing the back of the subject. This difference in height is calculated for a characteristic part specified as a part of the back of the subject for which the degree of curvature is to be measured. In Patent Document 2, there is a description that the degree of a twist of the characteristic part can be grasped in this manner.

PRIOR ART DOCUMENT(S)

Patent Document(s)

Patent Document 1: JP 2013-248089 A
Patent Document 2: WO 2013/81030 A1

SUMMARY OF THE INVENTION

Problem to be Solved by the Invention

However, the predetermined parameter described in Patent Document 1 is not an indicator representing a local twist of the back of the subject, and thus it is considered to be difficult to grasp the local twist of the back of the subject. Further, in the evaluation system for scoliosis described in Patent Document 2, it is difficult to grasp the degree of a twist for a part other than the specified characteristic part.

Therefore, both the systems described in Patent Documents 1 and 2 have a difficulty in completely grasping the local twist for the entire back of the subject. As described above, the back of the subject is locally twisted as the sign of scoliosis in many cases. Thus, even when any one of the systems described in Patent Documents 1 and 2 is used, the sign of scoliosis may fail to be detected.

This invention has been made in view of the above-mentioned circumstances, and has an object to provide a scoliosis diagnosis assistance device and the like, which are capable of assisting in detecting scoliosis in an early stage.

Means to Solve the Problem

A scoliosis diagnosis assistance device according to a first aspect of this invention comprises:

a first shape information acquisition module configured to acquire back shape information representing a three-dimensional shape of a back of a subject;

a second shape information acquisition module configured to acquire mirror-symmetry information representing a three-dimensional shape having a mirror-symmetry relationship with the three-dimensional shape of the back of the subject with respect to a sagittal plane of the three-dimensional shape;

a deviation distribution acquisition module configured to acquire a distribution of deviations between the three-dimensional shape represented by the acquired back shape information and the three-dimensional shape represented by the acquired mirror-symmetry information; and an output controller configured to cause an output device to output diagnosis assistance information for assisting in diagnosis of scoliosis for the subject, the diagnosis assistance information being information acquired based on the acquired distribution of deviations.

A scoliosis diagnosis assistance method according to a second aspect of this invention comprises acquiring back shape information representing a three-dimensional shape of a back of a subject;

acquiring mirror-symmetry information representing a three-dimensional shape having a mirror-symmetry relationship with the three-dimensional shape of the back of the subject with respect to a sagittal plane of the three-dimensional shape;

acquiring a distribution of deviations of an entire three-dimensional shape represented by the acquired back shape information from the three-dimensional shape represented by the acquired mirror-symmetry information; and causing an output device to output diagnosis assistance information for assisting in diagnosis of scoliosis for the subject, the diagnosis assistance information being information acquired based on the acquired distribution of deviations.

A program according to a third aspect of this invention is a program for causing a computer to function as:

a first shape information acquisition module configured to acquire back shape information representing a three-dimensional shape of a back of a subject;

a second shape information acquisition module configured to acquire mirror-symmetry information representing a three-dimensional shape having a mirror-symmetry relationship with the three-dimensional shape of the back of the subject with respect to a sagittal plane of the three-dimensional shape;

a deviation distribution acquisition module configured to acquire a distribution of deviations of an entire three-dimensional shape represented by the acquired back shape information from the three-dimensional shape represented by the acquired mirror-symmetry information; and an output controller configured to cause an output device to output diagnosis assistance information for assisting in diagnosis of scoliosis for the subject, the diagnosis assistance information being information acquired based on the acquired distribution of deviations.

Effect of the Invention

According to this invention, the diagnosis assistance information, which is obtained based on the distribution of deviations between the three-dimensional shape of the back of the subject and the three-dimensional shape having a mirror-symmetry relationship with the three-dimensional shape of the back of the subject with respect to the sagittal plane thereof, is output to the output device. With this, for example, a doctor in charge of diagnosis can observe the local twist of the back of the subject by referring to the diagnosis assistance information output to the output device. In this manner, it is possible to assist in detecting the local twist, to thereby assist in detecting scoliosis in an early stage.

BRIEF DESCRIPTION OF THE DRAWING

FIG. 11 includes images for showing examples of a distribution of deviations of the subject suffering from scoliosis, in which (a), (b), (c), and (d) relate to the first subject, the second subject, the third subject, and the fourth subject, respectively.

FIG. 19 includes (a) which is an image for showing a region of interest in the second embodiment, and (b) which is an image for showing an example of a distribution of deviations of the same subject as that in (a).

FIG. 26 is a figure for showing a likelihood ratio in a case where the first and second asymmetric indices are both applied to each of the diagnosis of whether the Cobb angle represents scoliosis of 25 degrees or more and the diagnosis of whether the Cobb angle represents scoliosis of 15 degrees or more.

MODES FOR EMBODYING THE INVENTION

Embodiments of this invention are described with reference to the drawings.

First Embodiment

Figure 1:
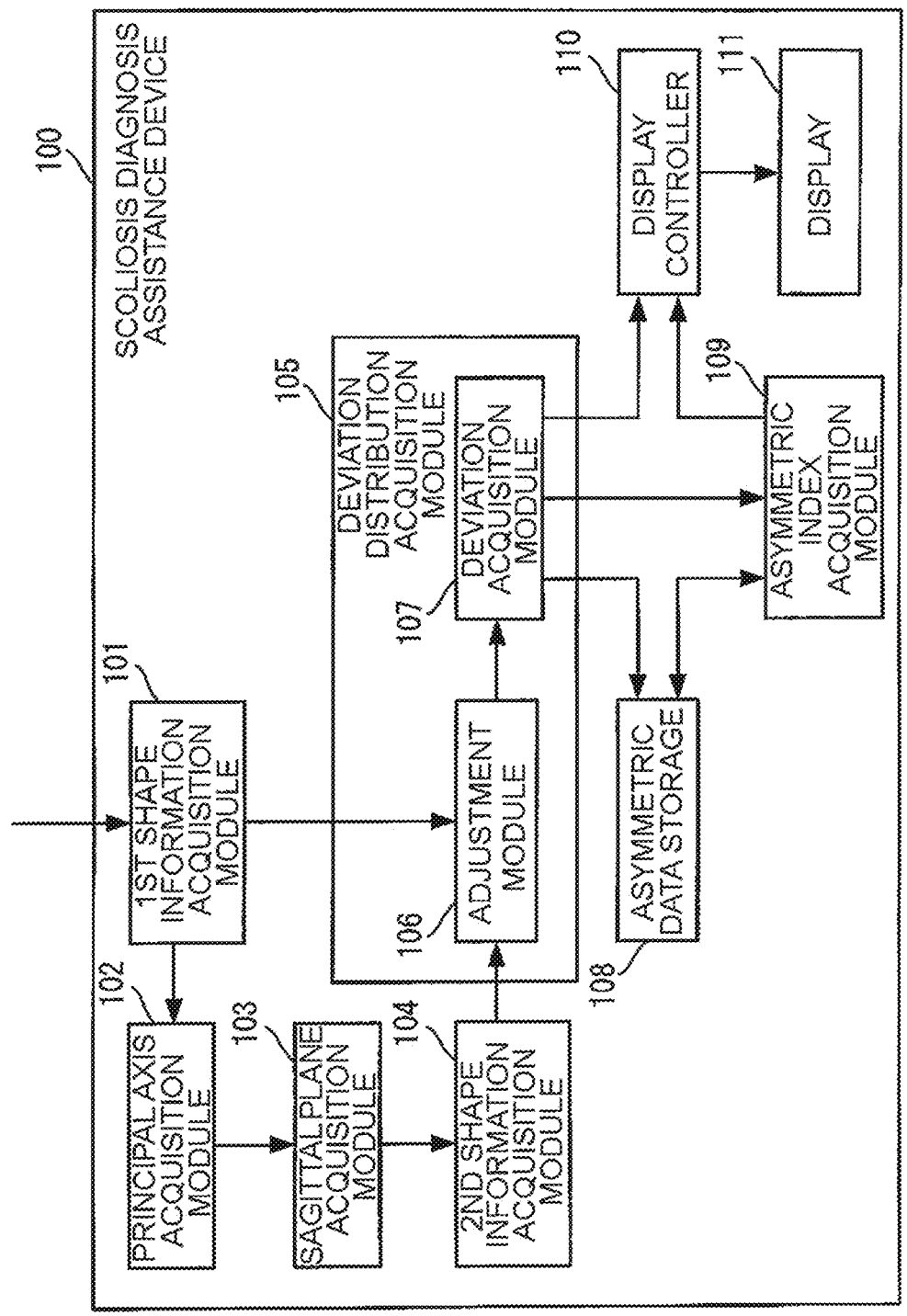
FIG. 1 is a diagram for illustrating a functional configuration of a scoliosis diagnosis assistance device according to a first embodiment of this invention.

A scoliosis diagnosis assistance device 100 according to a first embodiment of this invention is a device for assisting in diagnosis by a doctor of whether a patient is suffering from scoliosis or whether equipment for treating scoliosis is required. As illustrated in FIG. 1, from a functional point of view, the scoliosis diagnosis assistance device 100 includes a first shape information acquisition module 101, a principal axis acquisition module 102, a sagittal plane acquisition module 103, a second shape information acquisition module 104, a deviation distribution acquisition module 105, an asymmetric data storage 108, an asymmetric index acquisition module 109, a display controller 110, and a display 111.

The first shape information acquisition module 101 acquires back shape information. The back shape information is information representing a three-dimensional shape of the back of a subject. The back shape information in the first embodiment represents a back mesh. The back mesh represents a three-dimensional shape of the back of the subject by a set of surfaces of polygons, for example, a triangle. The back of the subject is a region whose surface shape changes due to scoliosis within a back appearance of the subject, and is typically a region (excluding arm) that extends from the waist to the shoulder.

Figure 2:
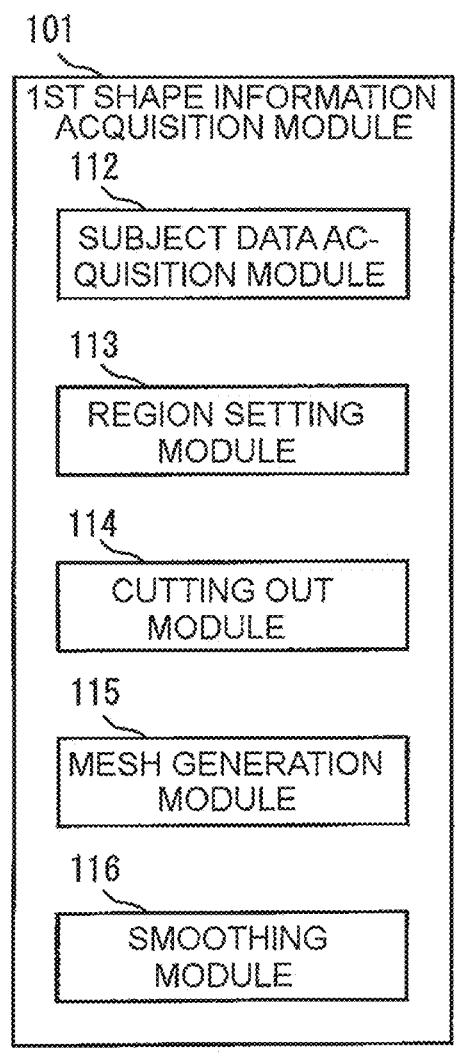
FIG. 2 is a diagram for illustrating a functional configuration of a first shape information acquisition module in the first embodiment of this invention.

Specifically, as illustrated in FIG. 2, the first shape information acquisition module 101 includes a subject data acquisition module 112, a region setting module 113, a cutting out module 114, a mesh generation module 115, and a smoothing module 116.

The subject data acquisition module 112 acquires subject data. The subject data contains scan data and color image data on the back appearance of the subject.

The scan data is data representing a three-dimensional shape of the back appearance of the subject with a plurality of points, and is, for example, generated by a 3D scanner. The 3D scanner is a device configured to detect unevenness of the surface of an object, and generate three-dimensional data representing the result of detection. The color image data is data representing a color image of the back appearance of the subject, and for example, may be generated by a camera, or may be generated by an RGB-D camera, which is configured to acquire a color image and a depth image at the same time, at the same time as the scan data.

The back appearance of the subject represented by each of the scan data and color image data acquired by the subject data acquisition module 112 is assumed to be the same posture, and the subject is more desirably folding hands, and standing or bending forward with both arms being extended.

The region setting module 113 sets a region of interest based on a color image of the back appearance of the subject, which is represented by the color image data acquired by the subject data acquisition module 112, and a hue threshold value determined in advance. The region of interest is a region to be used for assisting in diagnosis of the subject within the color image of the back appearance of the subject.

Specifically, the region setting module 113 compares the color image of the back appearance of the subject, which is represented by the color image data acquired by the subject data acquisition module 112, with the hue threshold value determined in advance. With this, the region setting module 113 extracts a back region from the color image of the back appearance of the subject, and sets the extracted back region as the region of interest. The back region is a region corresponding to the back of the subject, and in the first embodiment, it is assumed that the back region is adopted as the region of interest.

For example, scanning by a 3D scanner or photographing by a camera is performed under a state in which the subject exposes his or her skin of the back, for example, under a state in which the subject is shirtless. Thus, the region setting module 113 can extract a back region by identifying a skin color region. That is, for example, a value of a hue corresponding to a skin color is set as the hue threshold value.

As described above, the back appearance of the subject is assumed to be the subject folding hands, and standing or bending forward with both arms being extended. That is, the back appearance of the subject does not contain the arms of the subject, and thus the back region extracted by the region setting module 113 does not also contain the arms of the subject.

Processing to be executed by the region identification module 113 may be performed manually by a user with, for example, an input device (not shown). Under this assumption, the back appearance of the subject represented by the scan data or color image data may not be the subject folding hands, and standing or bending forward with both arms being extended.

The cutting out module 114 cuts out a plurality of points representing the shape of the back of the subject from the scan data acquired by the subject data acquisition module 112 based on the region of interest set by the region setting module 113.

The mesh generation module 115 generates the back shape information based on the plurality of points cut out by the cutting out module 114. The back shape information generated by the mesh generation module 115 in the first embodiment represents, for example, a back mesh being a set of surfaces of a plurality of triangles having those plurality of points as vertices. The back mesh is not limited to surfaces of triangles, but may be surfaces of polygons such as those of a quadrangle or a pentagon.

The smoothing module 116 subjects the back mesh represented by the back shape information, which is generated by the mesh generation module 115, to smoothing processing such as median filtering processing or moving average filtering processing. The smoothing module 116 outputs back shape information representing the back mesh subjected to the smoothing processing.

Referring back to FIG. 1, the principal axis acquisition module 102 subjects the back mesh represented by the back shape information, which is acquired by the first shape information acquisition module 101, to principal component analysis. With this, the principal axis acquisition module 102 acquires three principal axes included in a group of vertices forming the back mesh.

The three principal axes included in the group of vertices forming the back mesh are principal axes, which are a first axis, a second axis, and a third axis of the subject in a space having the group of vertices forming the back mesh represented by the back shape information. The first axis, the second axis, and the third axis of the subject are principal axes parallel to an up-down direction, a left-right direction, and a front-back direction of the subject, respectively.

The sagittal plane acquisition module 103 acquires a sagittal plane of the back mesh represented by the back shape information, which is acquired by the first shape information acquisition module 101. The sagittal plane of the back mesh is one example of the sagittal plane in a three-dimensional shape represented by the back shape information, and is a plane corresponding to the sagittal plane of the subject in the space having the group of vertices forming the back mesh.

Specifically, the sagittal plane acquisition module 103 acquires the sagittal plane of the back mesh based on the three principal axes acquired by the principal axis acquisition module 102.

The second shape information acquisition module 104 acquires mirror-symmetry information. The mirror-symmetry information is information representing a three-dimensional shape having a mirror-symmetry relationship with the back mesh of the subject with respect to the sagittal plane of that back mesh.

Specifically, the second shape information acquisition module 104 acquires the mirror-symmetry information based on the back mesh represented by the back shape information, which is acquired by the first shape information acquisition module 101, and the sagittal plane of the back mesh, which is acquired by the sagittal plane acquisition module 103. The mirror-symmetry information in the first embodiment represents a mirror-symmetric mesh. The mirror-symmetric mesh represents a three-dimensional shape being a set of surfaces of triangles, which are the same surfaces of polygons as those of the back mesh, and having a mirror-symmetry relationship with the back mesh of the subject with respect to the sagittal plane of that back mesh.

The deviation distribution acquisition module 105 acquires a distribution of deviations between the back mesh represented by the back shape information, which is acquired by the first shape information acquisition module 101, and the mirror-symmetric mesh represented by the mirror-symmetry information, which is acquired by the second shape information acquisition module 104.

Specifically, the deviation distribution acquisition module 105 includes an adjustment module 106 and a deviation acquisition module 107, and identifies a plurality of points at which the entire back mesh and the mirror-symmetric mesh correspond to each other to acquire respective distances between those corresponding points as the distribution of deviations.

The adjustment module 106 adjusts a positional relationship between the back mesh and the mirror-symmetric mesh. The back mesh and the mirror-symmetric mesh whose positional relationship is to be adjusted by the adjustment module 106 are acquired by the first shape information acquisition module 101 and the second shape information acquisition module 104, respectively.

Figure 3:
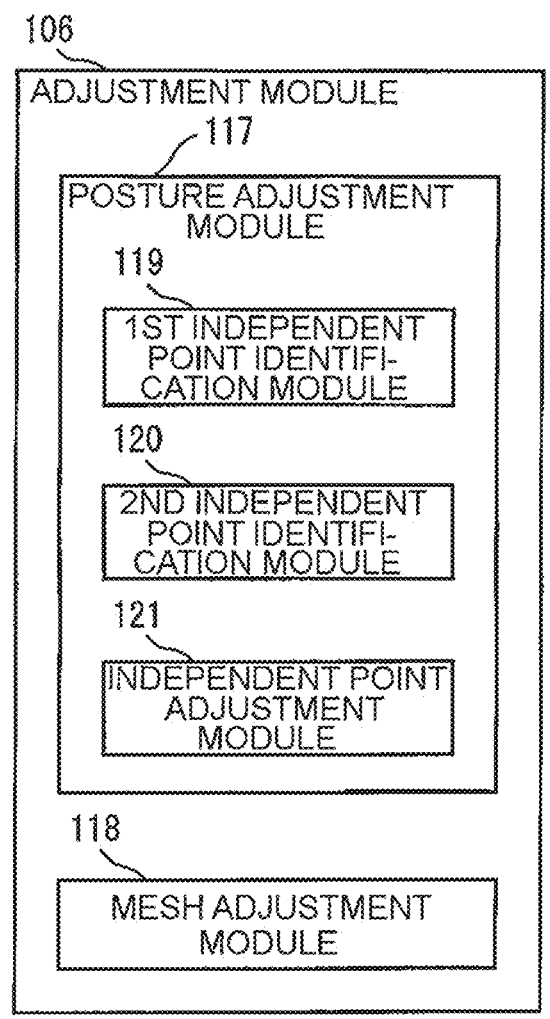
FIG. 3 is a diagram for illustrating a functional configuration of an adjustment module in the first embodiment of this invention.

More specifically, as illustrated in FIG. 3, the adjustment module 106 includes a posture adjustment module 117 and a mesh adjustment module 118.

The posture adjustment module 117 identifies a plurality of specific points (e.g., three specific points) for each of the back mesh and the mirror-symmetric mesh. Then, the posture adjustment module 117 adjusts the positional relationship between the back mesh and the mirror-symmetric mesh so that those three specific points match each other. With this, the positional relationship between the back mesh and the mirror-symmetric mesh is roughly adjusted.

More specifically, the posture adjustment module 117 includes a first independent point identification module 119, a second independent point identification module 120, and an independent point adjustment module 121.

The first independent point identification module 119 identifies a plurality of specific points on the back mesh. For example, the first independent point identification module 119 identifies, as specific points, points whose approximated absolute curvature is equal to or larger than a threshold value determined in advance on the back mesh and that are away from each other by a predetermined distance or more.

The second independent point identification module 120 identifies a plurality of specific points on the mirror-symmetric mesh. For example, the second independent point identification module 120 identifies, as specific points, points whose approximated absolute curvature is equal to or larger than a threshold value determined in advance on the mirror-symmetric mesh and that are away from each other by a predetermined distance or more.

One or both of specific points of the back mesh and the mirror-symmetric mesh may be specified by the user with, for example, an input device (not shown).

The independent point adjustment module 121 converts the posture and position of the back shape information so that the respective plurality of specific points identified by the first independent point identification module 119 and the second independent point identification module 120 match each other.

The mesh adjustment module 118 adjusts the positional relationship between the back mesh and the mirror-symmetric mesh, which has been roughly adjusted by the posture adjustment module 117, with an iterative closest point (ICP) method. With this, the positional relationship between the back mesh and the mirror-symmetric mesh is adjusted more accurately.

Referring back to FIG. 1, the deviation acquisition module 107 acquires a distribution of deviations of the entire back mesh, for which a positional relationship with the mirror-symmetric mesh has been adjusted by the adjustment module 106, from that mirror-symmetric mesh.

Specifically, the deviation acquisition module 107 identifies a plurality of corresponding points between the back mesh and the mirror-symmetric mesh whose positional relationship has been adjusted by the adjustment module 106, and acquires respective distances between those corresponding points as the distribution of deviations.

More specifically, the deviation acquisition module 107 identifies a combination of points of the back mesh and the mirror-symmetric mesh, which are positioned closest to each other, as the plurality of corresponding points. In the first embodiment, a combination of a plurality of vertices positioned closet to each other among a plurality of vertices contained in the back mesh and the mirror-symmetric mesh is identified as the plurality of corresponding points.

Then, the deviation acquisition module 107 acquires respective distances between the plurality of identified corresponding points as the distribution of deviations.

The asymmetric data storage 108 stores asymmetric data. The asymmetric data is data indicating a distribution of deviations acquired by the deviation distribution acquisition module 105.

The asymmetric index acquisition module 109 acquires the first asymmetric index based on the distribution of deviations acquired by the deviation distribution acquisition module 105 and the entire area of the back mesh. The first asymmetric index is a value indicating a degree to which the shape of the back of the subject is asymmetric.

The display controller 110 displays an image on the display 111. The display 111 displays an image under control by the display controller 110.

For example, the display controller 110 displays the distribution of deviations acquired by the deviation acquisition module 107 on the display 111 with, for example, a color map image. The color map image is an image in which the three-dimensional shape of the back of the subject is colored with a color determined in advance depending on the deviation.

Further, for example, the display controller 110 displays the first asymmetric index acquired by the asymmetric index acquisition module 109 on the display 111.

The "distribution of deviations" acquired by the deviation acquisition module 107, the "color map image" obtained based on the distribution of deviations, and the "first asymmetric index" obtained based on the distribution of deviations are each an example of diagnosis assistance information for assisting in diagnosis of scoliosis for the subject. The display controller 110 may display at least one of the distribution of deviations, the color map image, or the first asymmetric index on the display 111.

Further, the display controller 110 is an example of an output controller, and the display 111 is an example of an output device. For example, the output device is a printer or a communication interface for transmitting data to other devices, and the output controller may be a controller for controlling those devices.

The configuration of the scoliosis diagnosis assistance device 100 according to the first embodiment of this invention has been described. Now, an example of an operation of the scoliosis diagnosis assistance device 100 according to the first embodiment is described.

Figure 4:
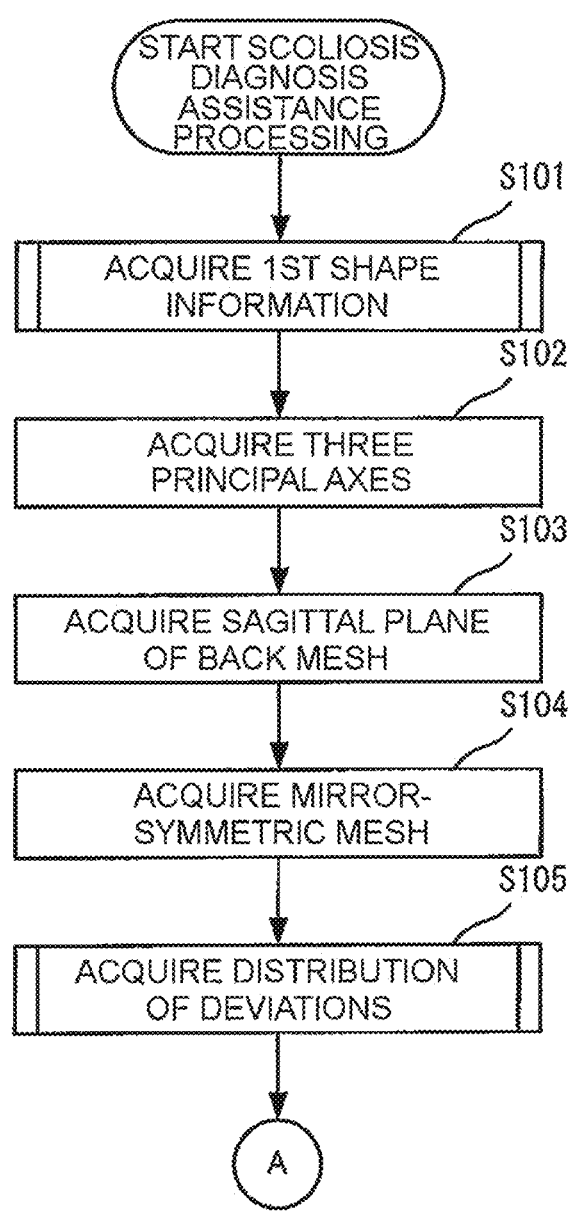
FIG. 4 is a flowchart for illustrating a flow of scoliosis diagnosis assistance processing in the first embodiment of this invention.
Figure 5:
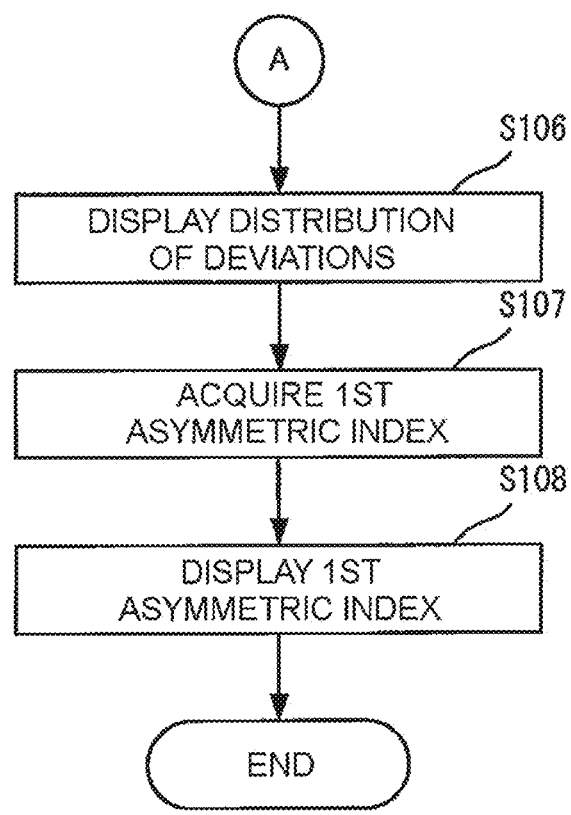
FIG. 5 is a flowchart for illustrating a flow of the scoliosis diagnosis assistance processing in the first embodiment of this invention.

The scoliosis diagnosis assistance device 100 executes scoliosis diagnosis assistance processing illustrated in FIG. 4 and FIG. 5. The scoliosis diagnosis assistance processing is processing for assisting in diagnosis of scoliosis. The scoliosis diagnosis assistance processing is started in response to, for example, the user operating the input device (not shown) to give a predetermined instruction. The input device is a part to be operated by the user for input, and is formed of, for example, buttons.

The first shape information acquisition module 101 acquires the back shape information (Step S101).

Figure 6:
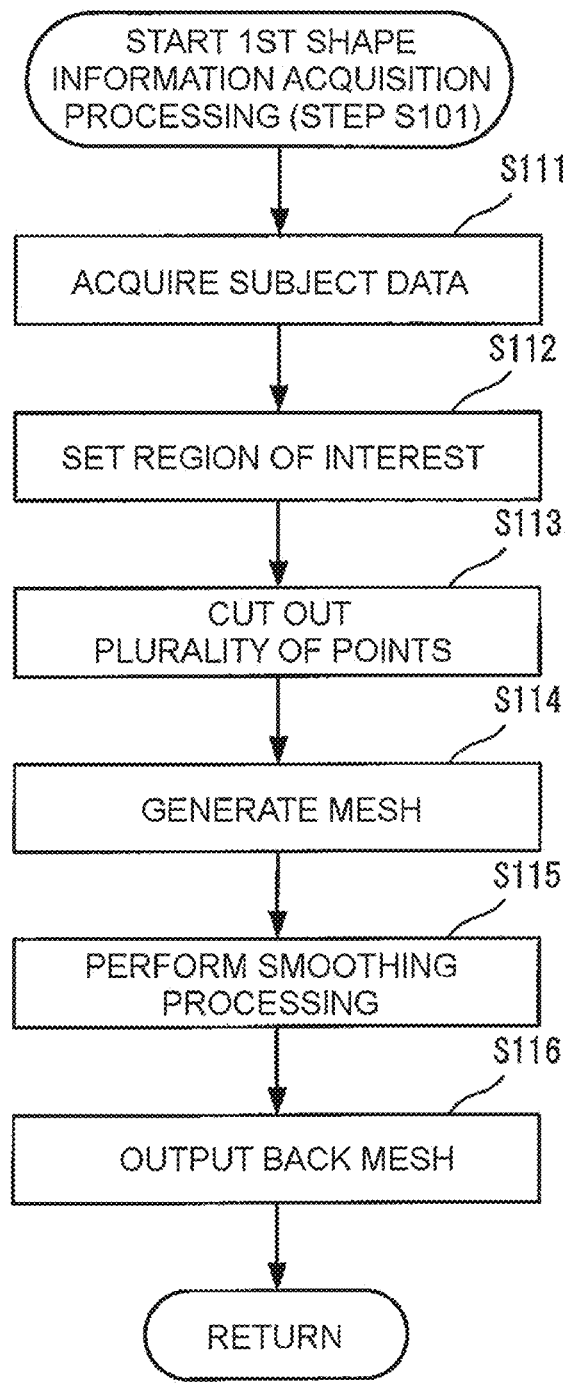
FIG. 6 is a flowchart for illustrating a flow of first shape information acquisition processing in the first embodiment.

Specifically, as illustrated in FIG. 6, the subject data acquisition module 112 acquires subject data containing scan data and color image data on the back appearance of the subject (Step S111).

The region setting module 113 compares the color image acquired in Step S111 with the hue threshold value determined in advance, and extracts a back region corresponding to the back of the subject from the color image of the back appearance of the subject based on a result of comparison. The region setting module 113 sets the extracted back region as the region of interest (Step S112).

The cutting out module 114 cuts out a plurality of points representing the shape of the back of the subject from the scan data acquired in Step S111 based on the region of interest set in Step S112 (Step S113).

For example, the cutting out module 114 acquires region of interest information representing the region of interest set by the region setting module 113. The cutting out module 114 extracts a point contained in a region indicated by the acquired region of interest information from among a plurality of points contained in the scan data.

The mesh generation module 115 generates the back shape information representing the back mesh based on the plurality of points cut out by the cutting out module 114 (Step S114).

The smoothing module 116 subjects the back mesh generated in Step S114 to smoothing processing (Step S115).

The smoothing module 116 outputs the back shape information representing the back mesh subjected to the smoothing processing (Step S116). Examples of the back mesh acquired in this manner are shown in FIG. 10($a$) to FIG. 10($d$).

Figure 10:
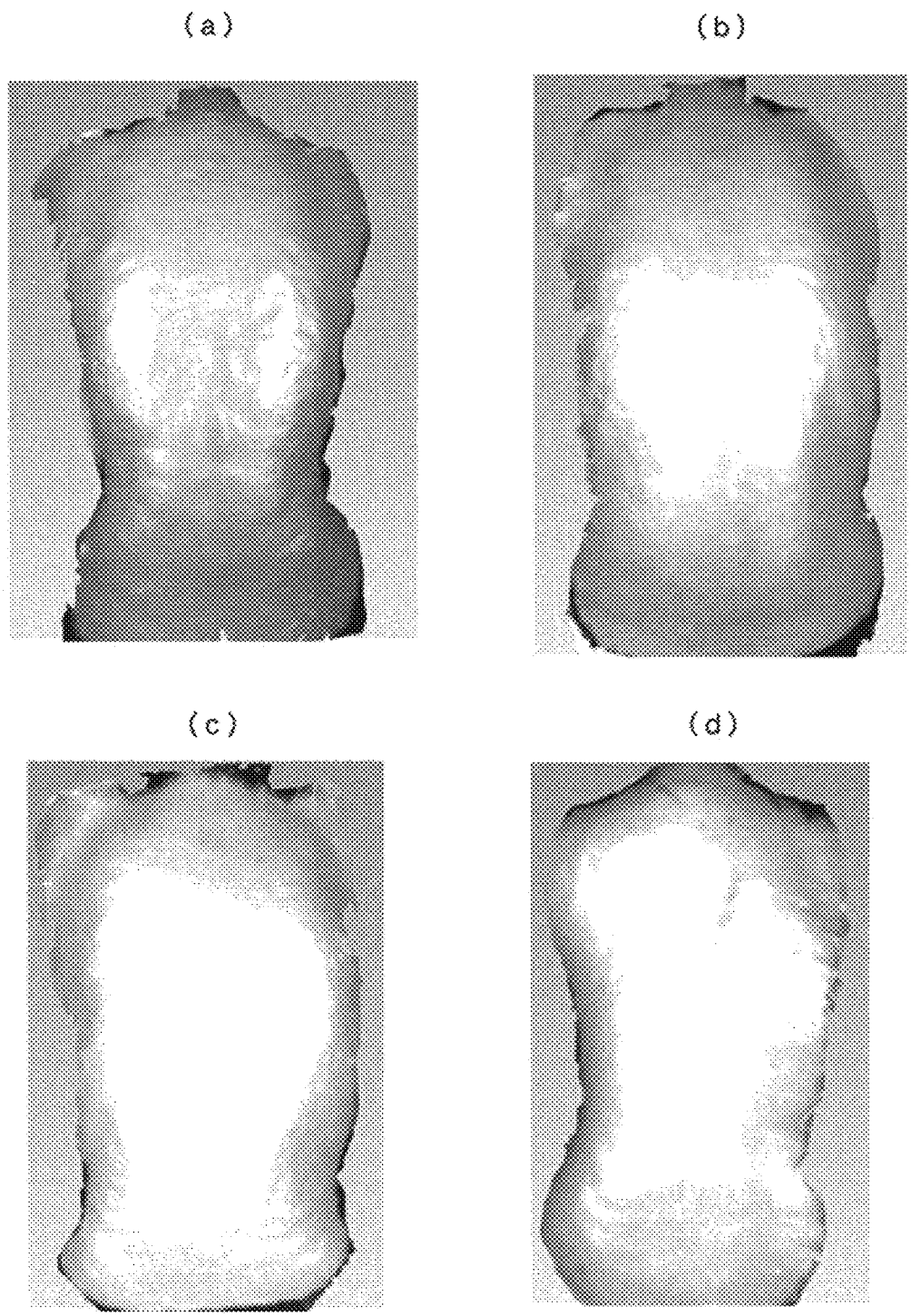
FIG. 10 includes images for showing examples of a back mesh of a subject suffering from scoliosis, in which (a), (b), (c), and (d) relate to a first subject, a second subject, a third subject, and a fourth subject, respectively.

FIG. 10($a$) to FIG. 10($d$) are images for showing examples of the back meshes of first to fourth subjects. The first subject is a subject suffering from scoliosis of 10 degrees. The second subject is a subject suffering from scoliosis of 12 degrees. The third subject is a subject suffering from scoliosis of 34 degrees. The fourth subject is a subject suffering from scoliosis of 60 degrees.

Returning to the scoliosis diagnosis assistance processing illustrated in FIG. 4, the principal axis acquisition module 102 subjects the back mesh acquired in Step S101 to principal component analysis, to thereby acquire three principal axes of the back mesh (Step S102).

For example, the principal axis acquisition module 102 subjects a group of vertices of the back mesh to principal component analysis, to thereby acquire three principal axes of the back mesh.

Specifically, for example, the principal axis acquisition module 102 acquires eigenvectors of variance-covariance matrices as three principal axes for coordinate values of the plurality of vertices on the back mesh.

The range of vertices on the back mesh is generally wider in the up-down direction, the left-right direction, and the front-back direction in the stated order.

Thus, a vector corresponding to the largest eigenvalue among the eigenvalues of variance-covariance matrices is acquired as a principal axis corresponding to the first axis of the subject in a space having the group of vertices forming the back mesh. A vector corresponding to the second largest eigenvalue among the eigenvalues of variance-covariance matrices is acquired as a principal axis corresponding to the second axis of the subject in the space having the group of vertices forming the back mesh. A vector corresponding to the smallest eigenvalue among the eigenvalues of variance-covariance matrices is acquired as a principal axis corresponding to the third axis of the subject in the space having the group of vertices forming the back mesh.

It suffices that the principal axis acquisition module 102 acquire at least two principal axes corresponding to the first principal axis and the third principal axis. In this case, the sagittal plane acquisition module 103 may acquire the sagittal plane of the back mesh based on the two principal axes acquired by the principal axis acquisition module 102. With this, the calculation amount becomes smaller compared to a case of acquiring the three axes, and thus it becomes possible to speed up the processing.

The sagittal plane acquisition module 103 acquires the sagittal plane of the back mesh based on the three axes acquired in Step S102 (Step S103).

The second shape information acquisition module 104 acquires the mirror-symmetry information representing the mirror-symmetric mesh based on the back mesh acquired in Step S101 and the sagittal plane acquired in Step S103 (Step S104).

Figure 27:
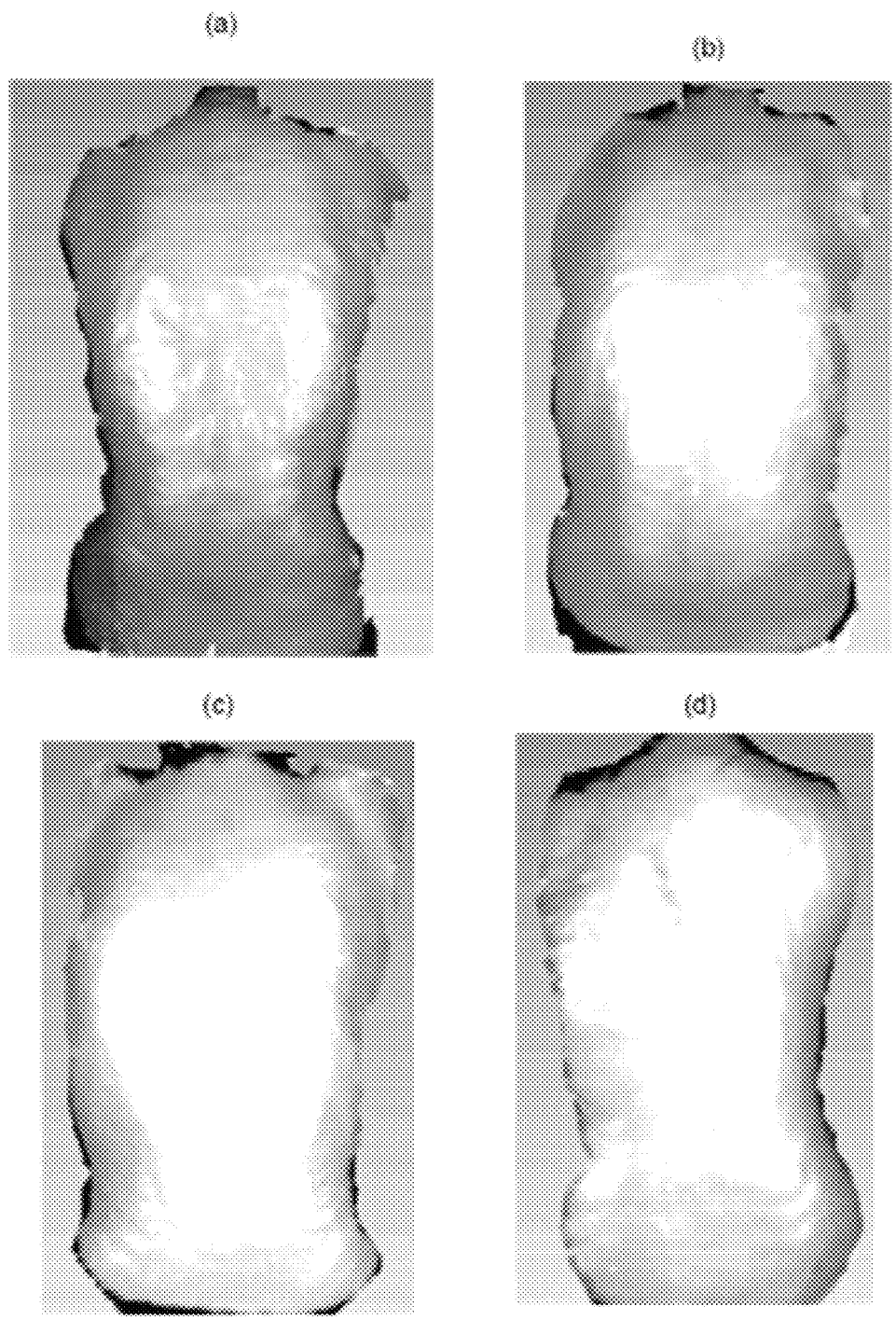
FIG. 27 includes images for showing examples of a mirror-symmetric mesh, in which (a), (b), (c), and (d) are created based on the back mesh represented by (a), (b), (c), and (d) of FIG. 10, respectively.

For example, the second shape information acquisition module 104 creates the mirror-symmetric mesh by subjecting the back mesh to mirror image transformation with respect to the sagittal plane. Here, FIG. 27(*a*) to FIG. 27(*d*) are images for showing examples of the mirror-symmetric mesh meshes of first to fourth subjects. That is, the mirror-symmetric mesh meshes shown in FIG. 27(*a*) to FIG. 27(*d*) are created based on the back mesh shown in Fig.10(*a*) to Fig.10(*d*), respectively.

For example, when there is no corresponding points on the mirror-symmetric mesh and the back mesh perpendicular to each other with respect to a coronal plane, and as a result, a point corresponding to the back mesh cannot be identified on the mirror-symmetric mesh, the mirror-symmetric mesh may be extended by, for example, extrapolation.

The deviation distribution acquisition module 105 acquires the distribution of deviations of the entire back mesh represented by the back shape information acquired in Step S101 from the mirror-symmetric mesh represented by the mirror-symmetry information acquired in Step S104 (Step S105).

Figure 7:
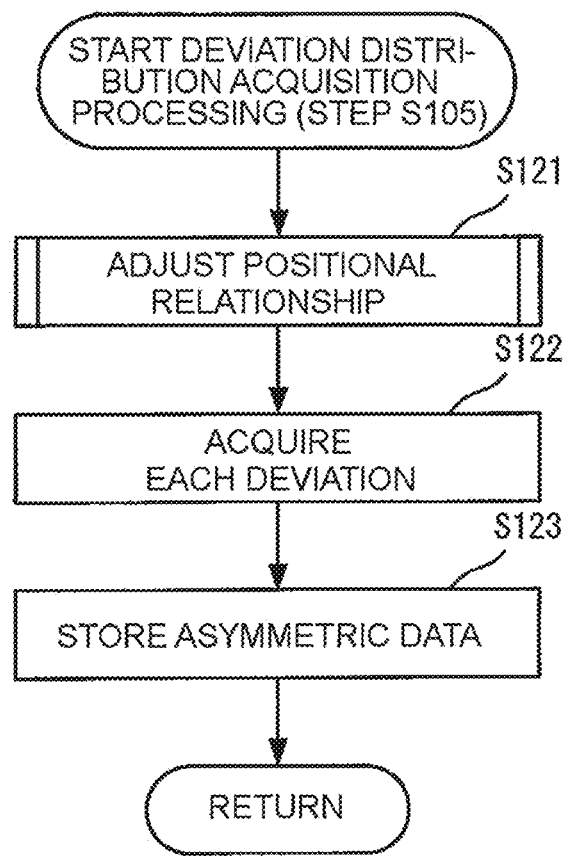
FIG. 7 is a flowchart for illustrating a flow of deviation distribution acquisition processing in the first embodiment.

Specifically, as illustrated in FIG. 7, the adjustment module 106 adjusts the positional relationship between the back mesh, which is represented by the information acquired in Step S101, and the mirror-symmetric mesh, which is represented by the information acquired in Step S104 (Step S121).

Figure 8:
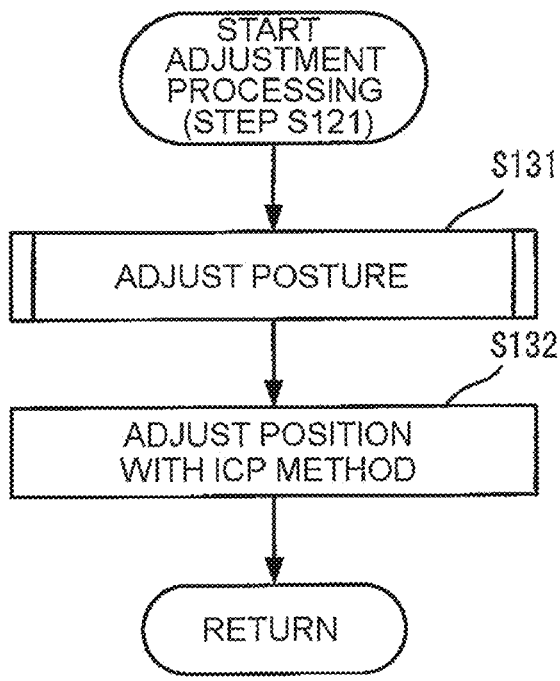
FIG. 8 is a flowchart for illustrating a flow of adjustment processing in the first embodiment.

More specifically, as illustrated in FIG. 8, the posture adjustment module 117 adjusts the postures of the back mesh and the mirror-symmetric mesh based on the plurality of specific points in each of the back mesh and the mirror-symmetric mesh (Step S131).

Figure 9:
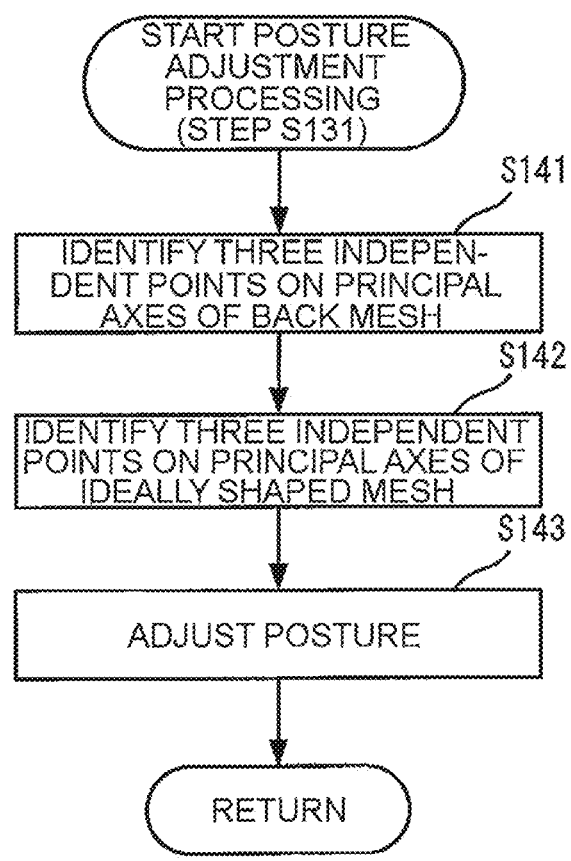
FIG. 9 is a flowchart for illustrating a flow of posture adjustment processing in the first embodiment.

More specifically, as illustrated in FIG. 9, the first independent point identification module 119 identifies, for example, three specific points on the back mesh (Step S141). Further, the second independent point identification module 120 identifies, for example, three specific points on the mirror-symmetric mesh (Step S142). The independent point adjustment module 121 adjusts the postures of the back mesh and the mirror-symmetric mesh so that positions of respective points identified in Step S141 and Step S142 match each other (Step S143).

Returning to the adjustment processing illustrated in FIG. 8, the mesh adjustment module 118 adjusts, with the ICP method, the positional relationship between the back mesh and the mirror-symmetric mesh whose positional relationship has been adjusted in Step S131 (Step S132). With this, the positional relationship between the back mesh and the mirror-symmetric mesh is adjusted more accurately.

Returning to the deviation distribution acquisition processing illustrated in FIG. 7, the deviation acquisition module 107 acquires deviations of the entire back mesh, whose positional relationship with the mirror-symmetric mesh has been adjusted in Step S132, from that mirror-symmetric mesh (Step S122).

The deviation acquisition module 107 stores asymmetric data indicating the distribution of deviations associating each deviation acquired in Step S107 with the position of each region into the asymmetric data storage 108 (Step S123).

Returning to the scoliosis diagnosis assistance processing illustrated in FIG. 5, the display controller 110 displays the distribution of deviations acquired in Step S105 on the display 111 by, for example, the color map image. With this, the display 111 displays the distribution of deviations on the back of the subject by the color map image (Step S106). Examples of the distribution of deviations displayed in this manner are shown in FIG. 11(*a*) to FIG. 11(*d*) and FIG. 12.

Figure 12:
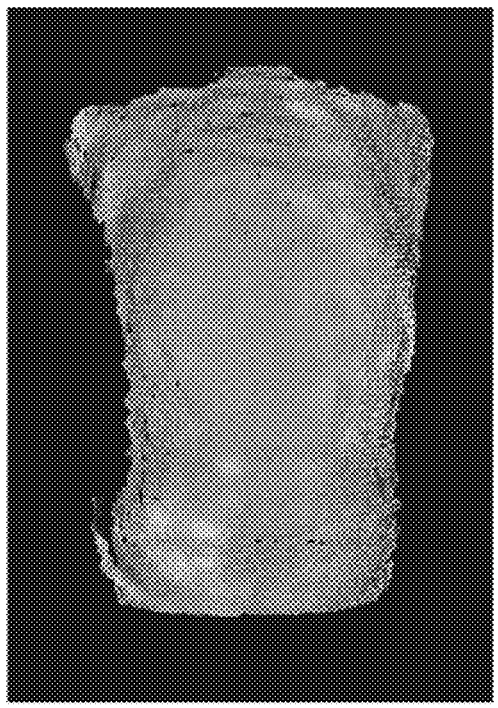
FIG. 12 is an image for showing an example of a distribution of deviations of a healthy subject.

FIG. 11(*a*) to FIG. 11(*d*) are images for showing examples of the distribution of deviations of the first to fourth subjects. FIG. 12 is an image for showing of an example of the distribution of deviations of a healthy subject represented by a color map image.

The asymmetric index acquisition module 109 acquires the first asymmetric index based on each deviation contained in the distribution of deviations acquired in Step S105 and the area of each mesh region contained in the entire back mesh (Step S107).

In the first embodiment, the asymmetric index acquisition module 109 acquires, as the first asymmetric index, a value obtained by dividing the sum of squares of deviations by the area of the entire mesh region on the back mesh, for example.

The first asymmetric index indicates 0 when the back mesh, namely, the shape of the back of the subject is completely symmetrical, and as the deviation from the symmetrical shape becomes larger, the first asymmetric index indicates a larger positive value. Further, when there is a narrow local portion on the back that extremely deviates from a symmetrical shape, the first asymmetric index tends to indicate a larger value by emphasizing the deviation in the local region.

The display controller 110 displays the first asymmetric index acquired in Step S107 on the display 111. With this, the display 111 displays the first asymmetric index (Step S108), and ends the scoliosis diagnosis assistance processing.

Figure 13:
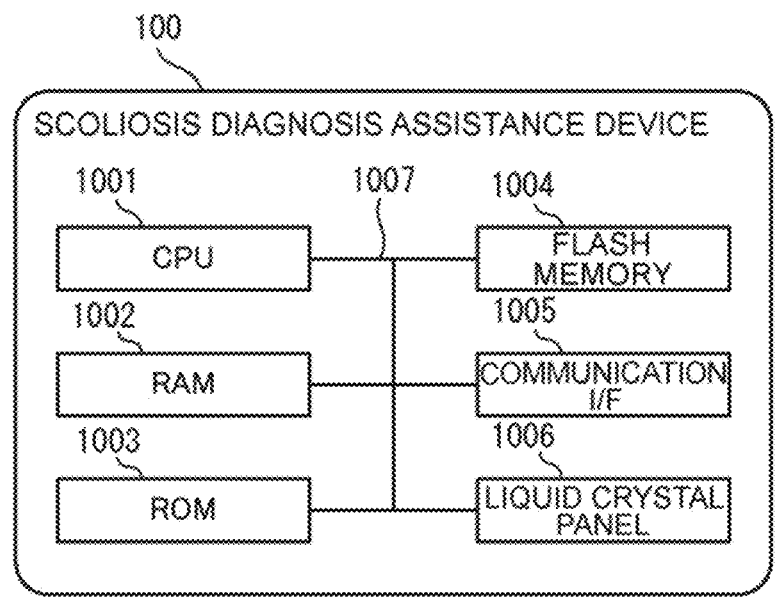
FIG. 13 is a diagram for illustrating an example of a physical configuration of the scoliosis diagnosis assistance device according to the first embodiment of this invention.

As illustrated in FIG. 13, the scoliosis diagnosis assistance device 100 according to the first embodiment physically includes, for example, a CPU (Central Processing Unit) 1001, a RAM (Random Access Memory) 1002, a ROM (Read Only Memory) 1003, a flash memory 1004, a communication I/F (Interface) 1005, and a liquid crystal panel 1006, which are communicably coupled to each other via an internal bus 1007. Such a scoliosis diagnosis assistance device 100 is, for example, a general-purpose personal computer, a tablet terminal, or a smartphone.

Each function included in the scoliosis diagnosis assistance device 100 is implemented by, for example, the CPU 1001 executing a pre-installed software program (hereinafter simply referred to as "program") in the RAM 1002 as a work space.

The program may be stored in a storage medium such as a flash memory, a DVD, or a CD-ROM for distribution, or may be distributed via a wired or wireless communication network or a communication network being a combination of wired and wireless communication networks, for example, the Internet.

Specifically, for example, the functions of the first shape information acquisition module 101, the principal axis acquisition module 102, the sagittal plane acquisition module 103, the second shape information acquisition module 104, the deviation distribution acquisition module 105, the asymmetric index acquisition module 109, and the display controller 110 are implemented by, for example, the CPU 1001 executing programs as described above.

The functions of the asymmetric data storage 108 are implemented by, for example, the flash memory 1004. The functions of the display 111 are implemented by, for example, the liquid crystal panel 1006.

The scoliosis diagnosis assistance device 100 may be a 3D scanner including such a physical configuration as described above. In this case, the scoliosis diagnosis assistance device 100 can acquire the scan data by its own operation.

The first embodiment of this invention has been described.

According to this invention, the diagnosis assistance information, which is obtained based on the distribution of deviations of the three-dimensional shape of the back of the subject from the three-dimensional shape having a mirror relationship with that three-dimensional shape with respect to the sagittal plane thereof, is displayed on the display 111. With this, for example, a doctor in charge of diagnosis can refer to the diagnosis assistance information displayed on the display 111 to observe the local twist of the back of the subject. In this manner, it is possible to assist in detecting the local twist, and thus assist in detecting scoliosis in an early stage.

According to the first embodiment, the back mesh representing the three-dimensional shape of the back of the subject and the mirror-symmetric mesh that depends on the back of the subject are acquired. Then, the acquired distribution of deviations of the entire back mesh from the mirror-symmetric mesh is displayed. With this, for example, a doctor in charge of diagnosis can refer to the distribution of deviations displayed on the display to observe the local twist of the entire back of the subject comprehensively. Therefore, it is possible to assist in detecting the local twist, and thus assist in detecting scoliosis in an early stage.

Further, the back mesh can be acquired by using, for example, a general 3D scanner. Thus, for example, a large-scale apparatus or radiation is not required to be used. Therefore, it is possible to provide the non-invasive scoliosis diagnosis assistance device 100 having a simple configuration.

The deviation acquisition module 107 identifies a plurality of corresponding points between the adjusted back mesh and the mirror-symmetric mesh, and acquires respective distances between the plurality of corresponding points as the distribution of deviations.

Specifically, the deviation acquisition module 107 in the first embodiment identifies a combination of vertices of the back mesh and the mirror-symmetric mesh, which are among a plurality of vertices forming the back mesh and a plurality of vertices forming the mirror-symmetric mesh and are positioned closest to each other, as the plurality of corresponding points. Then, the deviation acquisition module 107 acquires respective distances between the identified plurality of corresponding points as the distribution of deviations.

Through use of such a distance, it is possible to easily obtain the distribution of deviations of the entire back of the subject, and assist in detecting scoliosis in an early stage.

The second shape information acquisition module 104 acquires the mirror-symmetric mesh based on the back mesh and its sagittal plane. With this, it is possible to easily obtain the mirror-symmetric mesh that depends on the back of the subject, and assist in detecting scoliosis in an early stage.

The display controller 110 displays the distribution of deviations on the display 111 by the color map image obtained by coloring the image of the back of the subject with a color determined in advance depending on the deviation. With this, for example, a doctor in charge of diagnosis can easily grasp the three-dimensional twist of the back of the subject. Therefore, it is possible to assist in detecting scoliosis in an early stage.

The asymmetric index acquisition module 109 acquires the first asymmetric index indicating the degree of asymmetry of the shape of the back based on the deviations forming the distribution of deviations and the entire area of the back mesh. This first asymmetric index can be referred to, to thereby easily know the degree of deviation of the back of the subject from a symmetrical shape. Therefore, it is possible to assist in detecting scoliosis in an early stage.

The first shape information acquisition module 101 generates the back mesh by cutting out the back of the subject from the scan data on the back appearance of the subject based on the color image of the back appearance of the subject. With this, the back mesh can be acquired automatically. The scan data and the color image can be acquired easily by using a 3D scanner or a camera, and thus it is possible to easily obtain the distribution of deviations for the entire back of the subject, and assist in detecting scoliosis in an early stage.

After the adjustment module 106 has adjusted the positional relationship between the back mesh and the mirror-symmetric mesh based on the specific points, the adjustment module 106 adjusts the positional relationship between the back mesh and the mirror-symmetric mesh with the ICP method. With this, the positional relationship between the back mesh and the mirror-symmetric mesh can be adjusted accurately automatically, and it is possible to easily obtain the distribution of deviations for the entire back of the subject, and assist in detecting scoliosis in an early stage.

With this, in particular, an accurate distribution of deviations can be obtained without depending on the position and posture of the subject with respect to, for example, a 3D scanner for acquiring the back mesh. Therefore, it is possible to easily assist in detecting scoliosis in an early stage. For example, it is useful for the subject to bend forward for detection of scoliosis, and the distribution of deviations is obtained based on the back mesh of the subject bending forward, to thereby be able to assist in detecting scoliosis accurately, easily, and reliably in an early stage.

Second Embodiment

In the first embodiment, the back region extracted by the region setting module 113 is adopted as the region of interest as it is. In a second embodiment of this invention, a part of the back region is adopted as the region of interest. Further, in the second embodiment, a second asymmetric index obtained by dividing the first asymmetric index by the height of the subject is adopted as the diagnosis assistance information in addition to the first asymmetric index described in the first embodiment.

Figure 14:
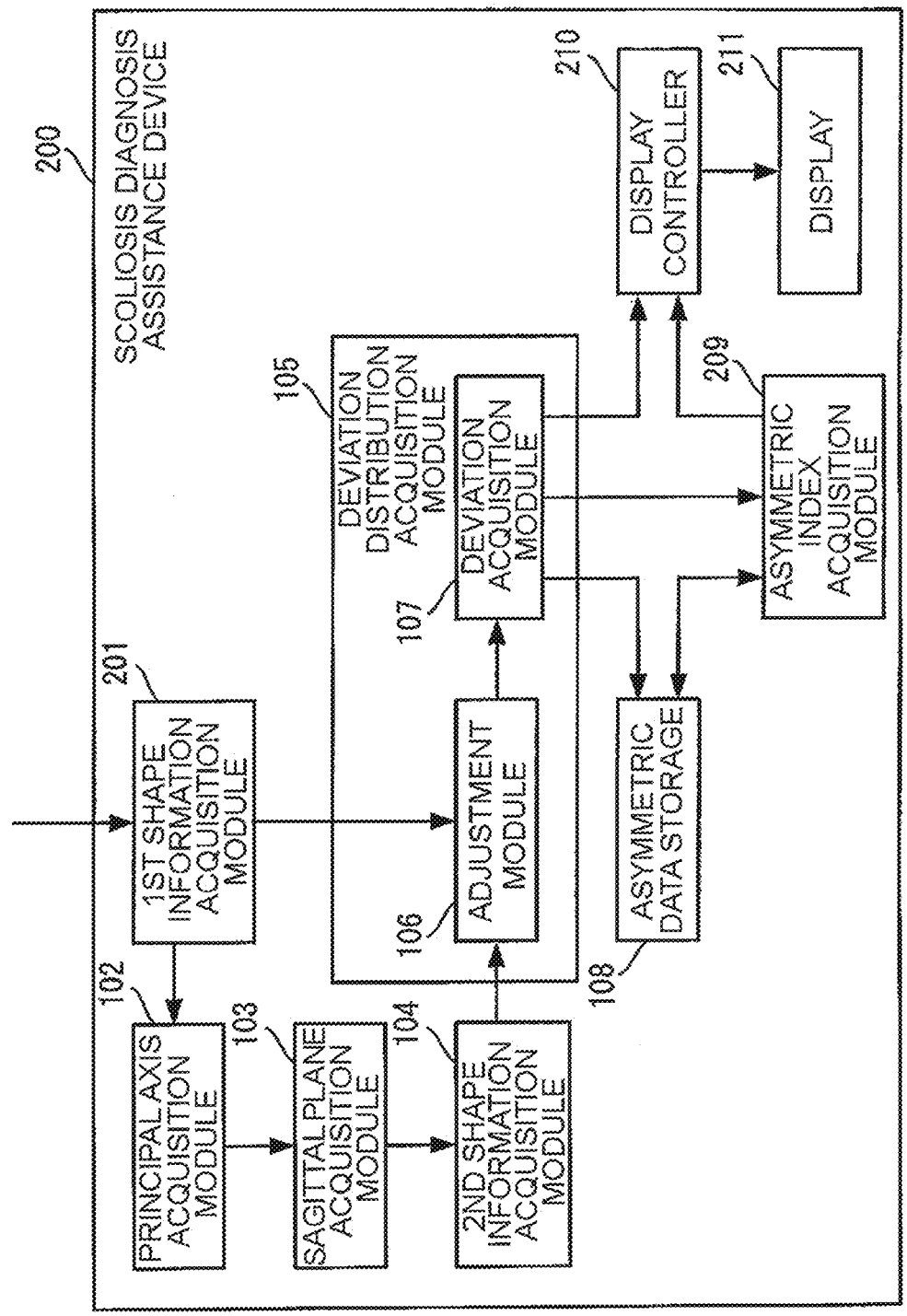
FIG. 14 is a diagram for illustrating an example of a functional configuration of a scoliosis diagnosis assistance device according to a second embodiment of this invention.

As illustrated in FIG. 14, from a functional point of view, a scoliosis diagnosis assistance device 200 according to the second embodiment includes the principal axis acquisition module 102, the sagittal plane acquisition module 103, the second shape information acquisition module 104, the deviation distribution acquisition module 105 including the adjustment module 106 and the deviation acquisition module 107, and the asymmetric data storage 108, which are similar to the components in the first embodiment.

Further, from a functional point of view, the scoliosis diagnosis assistance device 200 includes a first shape information acquisition module 201, an asymmetric index acquisition module 209, a display controller 210, and a display 211 instead of the first shape information acquisition module 101, the asymmetric index acquisition module 109, the display controller 110, and the display 111 in the first embodiment, respectively.

Similarly to the first shape information acquisition module 101 in the first embodiment, the first shape information acquisition module 201 acquires the back shape information representing the three-dimensional shape of the back of the subject.

Figure 15:
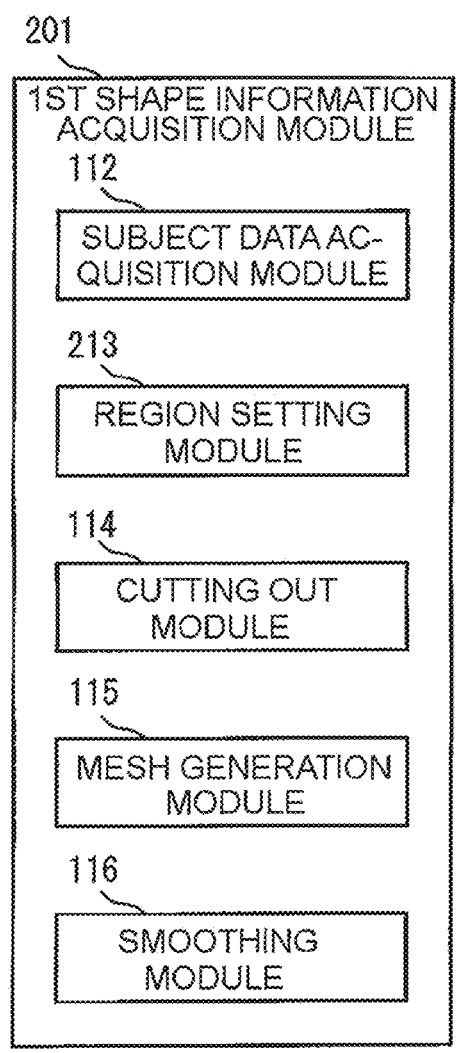
FIG. 15 is a diagram for illustrating a functional configuration of a first shape information acquisition module in the second embodiment.

Specifically, as illustrated in FIG. 15, the first shape information acquisition module 201 in the second embodiment includes the subject data acquisition module 112, the cutting out module 114, the mesh generation module 115, and the smoothing module 116 similarly to the first embodiment. Further, the first shape information acquisition module 201 includes a region setting module 213 instead of the region setting module 113 in the first embodiment.

Similarly to the region setting module 113 in the first embodiment, the region setting module 213 sets the region of interest based on the color image of the back appearance of the subject indicated by the color image data acquired by the subject data acquisition module 112 and the hue threshold value determined in advance. The region setting module 213 in the second embodiment adopts a region extracted from the back region of the subject with a predetermined method as the region of interest, unlike the region setting module 113 in the first embodiment.

Specifically, similarly to the first embodiment, the region setting module 213 extracts a back region within the color image of the back appearance of the subject based on the color image of the back appearance of the subject indicated by the color image data acquired by the subject data acquisition module 112 and the hue threshold value determined in advance.

Then, the region setting module 213 sets a partial region extracted from the back region with a method determined in advance by, for example, the user, as the region of interest.

Similarly to the asymmetric index acquisition module 109 in the first embodiment, the asymmetric index acquisition module 209 acquires the first asymmetric index of the subject based on the distribution of deviations acquired by the deviation distribution acquisition module 105 and the entire area of the back mesh. The asymmetric index acquisition module 209 further acquires the second asymmetric index of the subject by dividing the first asymmetric index by the value indicating the size of the body of the subject. In the second embodiment, the height of the subject is adopted as the value indicating the size of the body of the subject.

Similarly to the first asymmetric index, the second asymmetric index is a value indicating the degree of asymmetry of the shape of the back of the subject.

The user may input height information indicating the height of the subject by, for example, an input device (not shown). Further, for example, the first shape information acquisition module 201 may acquire subject data containing the height information, and the asymmetric index acquisition module 209 may acquire the height information from, for example, the first shape information acquisition module 201.

The display controller 210 displays an image on the display 211, and the display 211 displays the image under control by the display controller 210. In this respect, the display controller 210 and the display 211 are approximately similar to the display controller 110 and the display 111 in the first embodiment, respectively.

The display controller 210 displays the second asymmetric index on the display 211 in addition to the color map image and the first asymmetric index described in the first embodiment.

As described above, the second asymmetric index is information obtained based on the distribution of deviations. That is, the "second asymmetric index" is one type of diagnosis assistance information as in the case of each of the "distribution of deviations", the "color map image", and the "first asymmetric index". The display controller 210 may display at least one of the distribution of deviations, the color map image, the first asymmetric index, or the second asymmetric index on the display 111.

Further, each of the display controller 210 and the display 211 in the second embodiment is one example of the output controller and the output device similarly to the display controller 110 and the display 111 in the first embodiment.

The configuration of the scoliosis diagnosis assistance device 200 according to the second embodiment of this invention has been described. Now, an example of an operation of the scoliosis diagnosis assistance device 200 according to the second embodiment is described.

Figure 16:
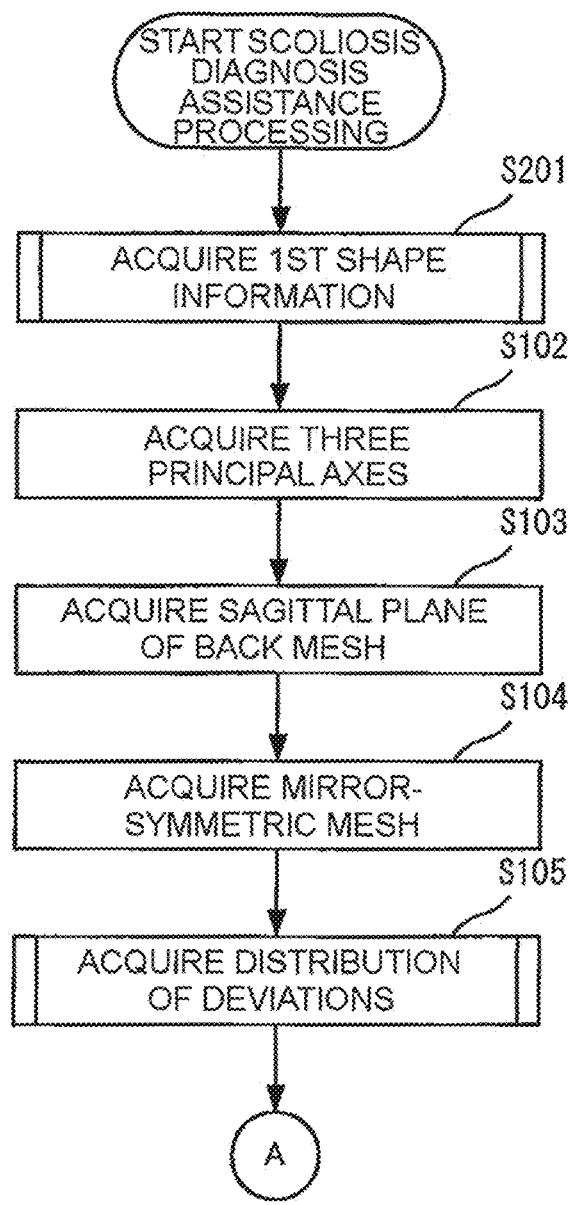
FIG. 16 is a flowchart for illustrating a flow of scoliosis diagnosis assistance processing in the second embodiment of this invention.
Figure 17:
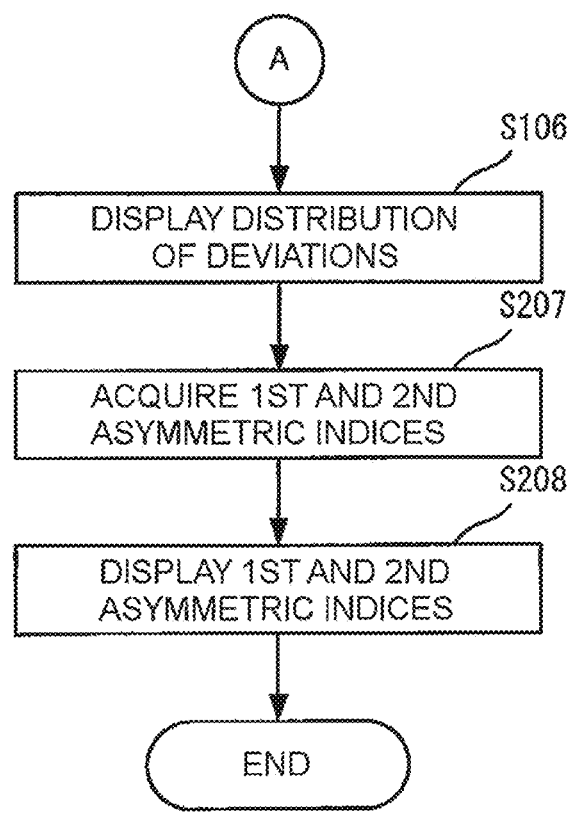
FIG. 17 is a flowchart for illustrating a flow of the scoliosis diagnosis assistance processing in the second embodiment of this invention.

Similarly to the first embodiment, the scoliosis diagnosis assistance device 200 executes scoliosis diagnosis assistance processing, which is processing of assisting in diagnosis of scoliosis. As illustrated in FIG. 16 and FIG. 17, the scoliosis diagnosis assistance processing in the second embodiment includes processing steps of Step S201, Step S207, and Step S208 instead of the respective processing steps of Step S101, Step S107, and Step S108 (refer to FIG. 4 and FIG. 5) in the first embodiment. Other processing steps (processing steps of Step S102 to Step S106) included in the scoliosis diagnosis assistance processing in the second embodiment are similar to the respective processing steps included in the first embodiment.

The first shape information acquisition module 201 acquires the back shape information (Step S201).

Figure 18:
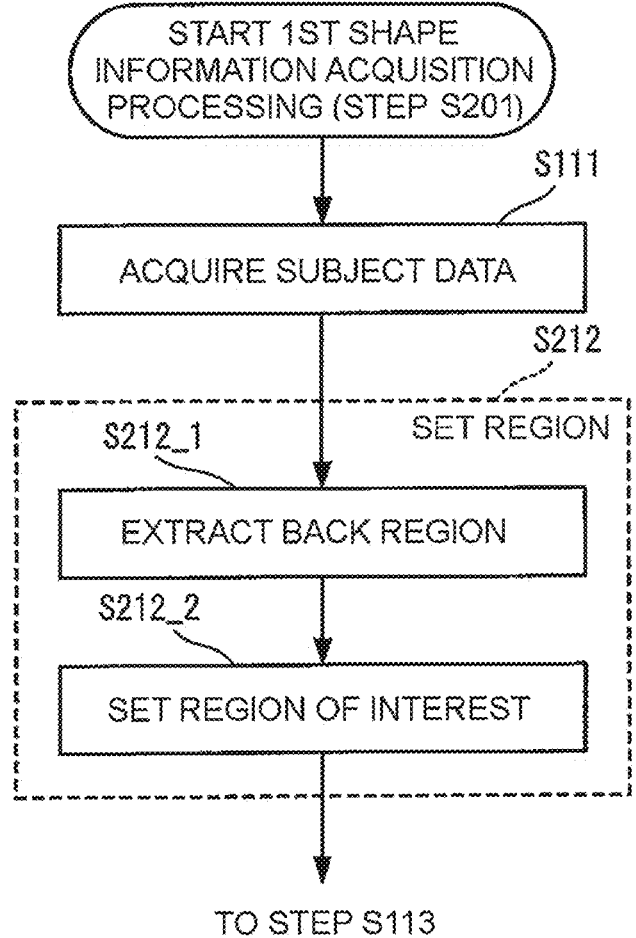
FIG. 18 is a flowchart for illustrating a part of first shape information acquisition processing in the second embodiment.

Specifically, as illustrated in FIG. 18, similarly to the first embodiment, the subject data acquisition module 112 acquires the subject data containing the scan data and color image data on the back appearance of the subject (Step S111).

The region setting module 213 compares the color image acquired in Step S111 with the hue threshold value determined in advance, and extracts a back region corresponding to the back of the subject from the color image of the back appearance of the subject based on a result of comparison (Step S212_1).

Further, the region setting module 113 sets a region identified from the extracted back region with the predetermined method as the region of interest (Step S212_2).

The method of identifying the region of interest may appropriately be set by, for example, the user. For example, in the second embodiment, the region of interest is determined in advance as a rectangular region within the back region, which is defined as 100% when the rectangular region ranges from the waist to both shoulders in the up-down direction and ranges from a central axis to the waistlines in the left-right direction. The central axis is a line that passes through the center of the left and right width of the back region. FIG. 19(a) is an image for showing, by a white rectangular frame W, an example of the region of interest (defined as 100% when ranging from central axis to waistlines) identified with such a method.

The cutting out module 114 executes cutting-out processing (Step S113) similar to that of the first embodiment based on the region of interest set in Step S112, and next, executes Step S114 to Step S116 similar to those of the first embodiment. Then, the scoliosis diagnosis assistance device 200 returns to the scoliosis diagnosis assistance processing illustrated in FIG. 16.

Then, as illustrated in FIG. 16 and FIG. 17, the processing steps of Step S102 to Step S106 are executed. FIG. 19(b) is an image for showing an example of the distribution of deviations of the subject displayed through the execution of the processing step of Step S106 in the second embodiment.

Next, as illustrated in FIG. 17, the asymmetric index acquisition module 209 acquires the first and second asymmetric indices based on each deviation contained in the distribution of deviations, the area of each mesh region contained in the entire back mesh, and the height of the subject (Step S207).

Specifically, for example, the asymmetric index acquisition module 209 acquires the first asymmetric index with a method similar to that of the first embodiment. Further, the asymmetric index acquisition module 209 acquires the second asymmetric index by dividing the first asymmetric index by the height of the subject.

The second asymmetric index is a value indicating a tendency approximately similar to the first asymmetric index described in the first embodiment.

Specifically, the second asymmetric index indicates 0 when the back mesh, namely, the shape of the back of the subject is completely symmetrical, and as the deviation from the symmetrical shape becomes larger, the second asymmetric index indicates a larger positive value. Further, when there is a narrow local portion on the back that extremely deviates from a symmetrical shape, the second asymmetric index tends to indicate a larger value by emphasizing the deviation in the local region.

The display controller 210 displays the first and second asymmetric indices acquired in Step S207 on the display 211. With this, the display 211 displays the first and second asymmetric indices (Step S208), and ends the scoliosis diagnosis assistance processing.

The scoliosis diagnosis assistance device 200 according to the second embodiment may be physically configured similarly to the scoliosis diagnosis assistance device 100 according to the first embodiment.

The second embodiment of this invention has been described.

According to this invention, similarly to the first embodiment, the diagnosis assistance information, which is obtained based on the distribution of deviations of the three-dimensional shape of the back of the subject from the three-dimensional shape having a mirror relationship with that three-dimensional shape with respect to the sagittal plane thereof, is displayed on the display 211. With this, for example, a doctor in charge of diagnosis can refer to the diagnosis assistance information displayed on the display 211 to observe the local twist of the back of the subject. In this manner, it is possible to assist in detecting the local twist, and thus assist in detecting scoliosis in an early stage.

In the second embodiment, not the entire back region but a part thereof is set as the region of interest. In general, the three-dimensional shape of the body surface near the edge of the back of the subject is susceptible to influence of the posture of the subject. Thus, a region (e.g., back region excluding the neighborhood of the edge of that back region) whose three-dimensional shape of the body surface is likely to change mainly due to twist of a spine can be set as the region of interest, to thereby obtain more accurate diagnosis assistance information. Further, a region extracted from the back region with the predetermined method can be set as the region of interest, to thereby set a region approximately similar between subjects irrespective of the conditions of photographing those subjects. Thus, it is possible to obtain an asymmetric index that can be compared among different subjects, and obtain an asymmetric index that is more useful for diagnosis of scoliosis. With this, it is possible to assist in detecting scoliosis in an early stage. Further, it is possible to reduce the calculation amount for acquiring the distribution of deviations.

As described above, the first asymmetric index and the second asymmetric index exhibit approximately similar tendencies in diagnosis assistance as values indicating the degree of scoliosis, but have different points. In the following, a description is given of the usefulness and nature of each of the first asymmetric index and the second asymmetric index based on the first and second asymmetric indices obtained for a plurality of subjects with the method substantially described in the second embodiment with reference to FIG. 22 to FIG. 26.

The following description and FIG. 22 to FIG. 26 are based on a result obtained by defining a region within the back region as 100% when the region ranges from the waist to both shoulders in the up-down direction and ranges from the central axis to the waistlines in the left-right direction, and setting a 70% rectangular region thereof with respect to the central axis in the left-right direction as the region of interest. This point is different from the second embodiment.

Figure 20:
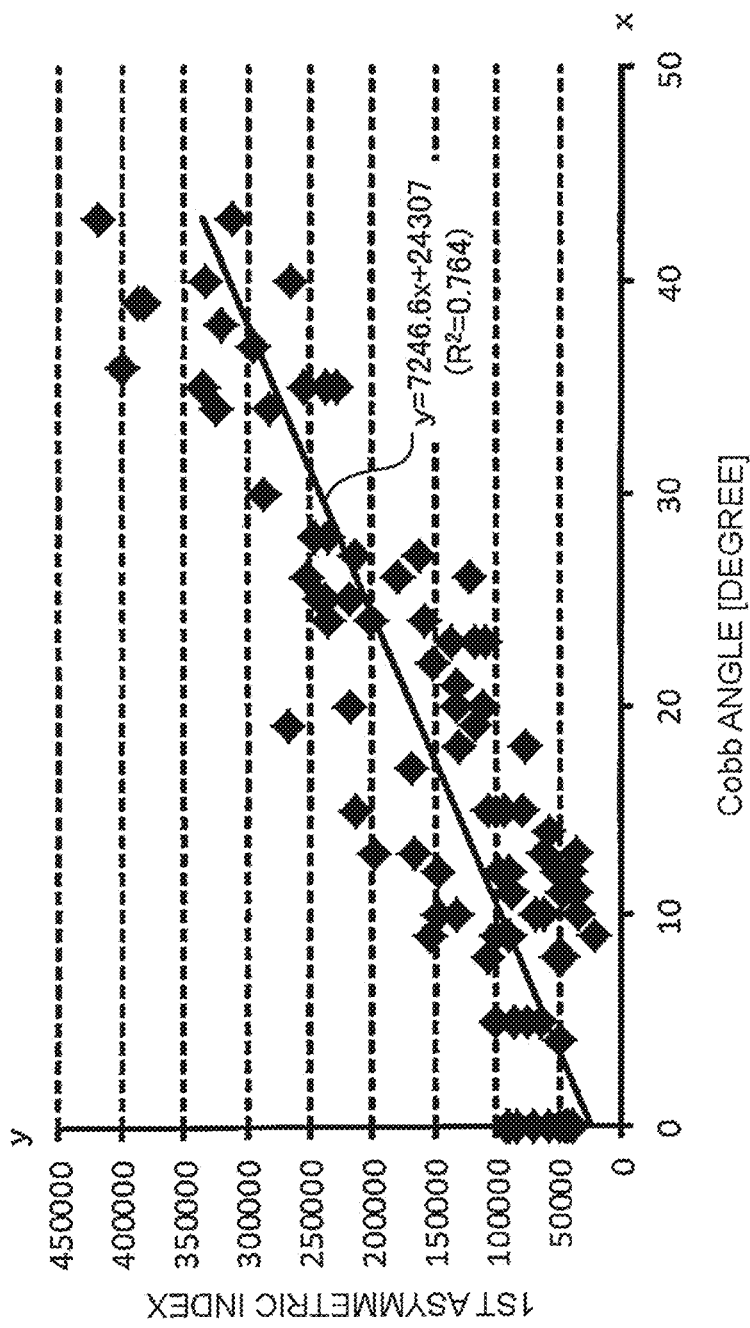
FIG. 20 is a figure for showing a relationship between a first asymmetric index and a Cobb angle, which is acquired by the scoliosis diagnosis assistance device according to the second embodiment.
Figure 21:
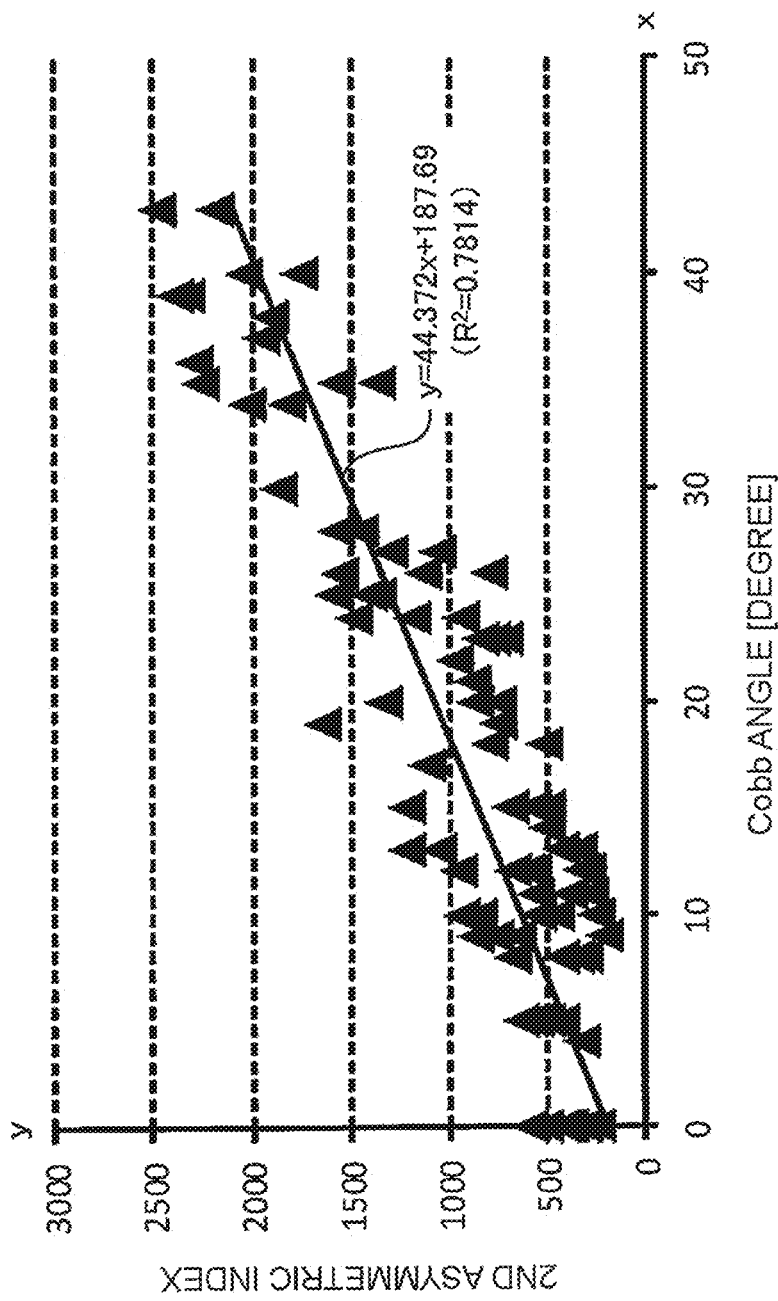
FIG. 21 is a figure for showing a relationship between a second asymmetric index and a Cobb angle, which is acquired by the scoliosis diagnosis assistance device according to the second embodiment.

FIG. 20 is a figure for showing a relationship between a Cobb angle and a first asymmetric index for a plurality of subjects. In FIG. 20, the horizontal axis (x-axis) represents the Cobb angle (unit: degree), and the vertical axis (y-axis) represents the first asymmetric index. FIG. 21 is a figure for showing a relationship between the Cobb angle and the second asymmetric index for a plurality of subjects. In FIG. 21, the horizontal axis (x-axis) represents the Cobb angle (unit: degree), and the vertical axis (y-axis) represents the first asymmetric index.

As shown in each of FIG. 20 and FIG. 21, when the correlation coefficient is denoted by R, $R^2$ indicates 0.764 in terms of the relationship between the Cobb angle and the first asymmetric index. Further, $R^2$ indicates 0.7814 in terms of the relationship between the Cobb angle and the second asymmetric index. The Cobb angle is generally adopted as an index indicating the degree of scoliosis. When the correlation coefficient R is observed, each of the first asymmetric index and the second asymmetric index is highly correlated with the Cobb angle, and is useful as an indicator indicating the degree of scoliosis.

Next, FIG. 22 to FIG. 25 are diagrams for illustrating (a) a receiver operating characteristic (ROC) curve and (b) a sensitivity, a false positive rate, a false negative rate, and a specificity in a case where each of the first and second asymmetric indices is applied to diagnosis of scoliosis. The straight line of the long dashed double-short dashed line of FIG. 22(a) to FIG. 25(a) indicates a line segment with an inclination of 45 degrees tangent to the ROC curve.

The "sensitivity" herein refers to a proportion of the asymmetric index indicating a positive value for a positive subject, and is also referred to as a "true positive sensitivity". The "false positive rate" herein refers to a proportion of the asymmetric index indicating a positive value for a negative subject. The "false negative rate" herein refers to a proportion of the asymmetric index indicating a negative value for a positive subject. The "specificity" herein refers to a proportion of the asymmetric index indicating a negative value for a negative subject.

Figure 22:
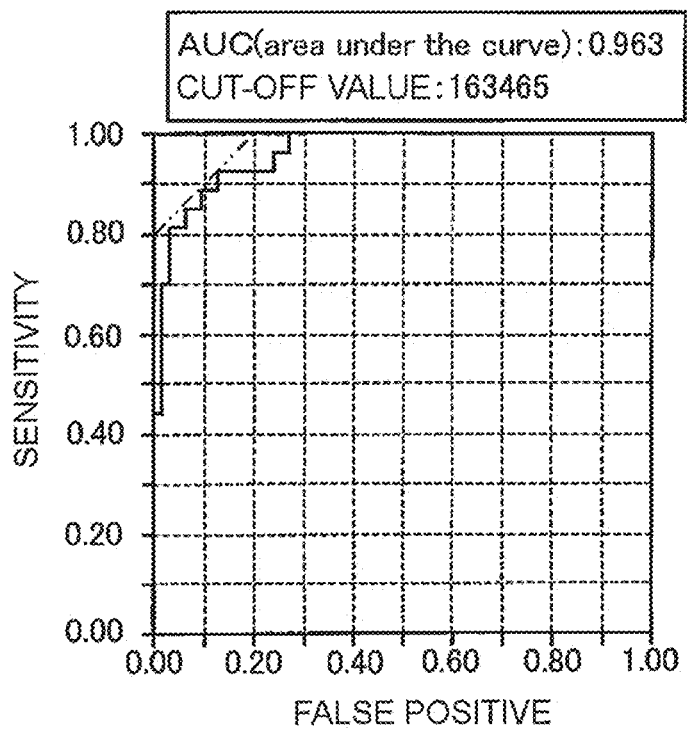
FIG. 22 includes diagrams for illustrating (a) an ROC curve and (b) a sensitivity, a false positive rate, a false negative rate, and a specificity in a case where the first asymmetric index acquired by the scoliosis diagnosis assistance device according to the second embodiment is applied to a diagnosis of whether the Cobb angle represents scoliosis of 25 degrees or more.
Figure 23:
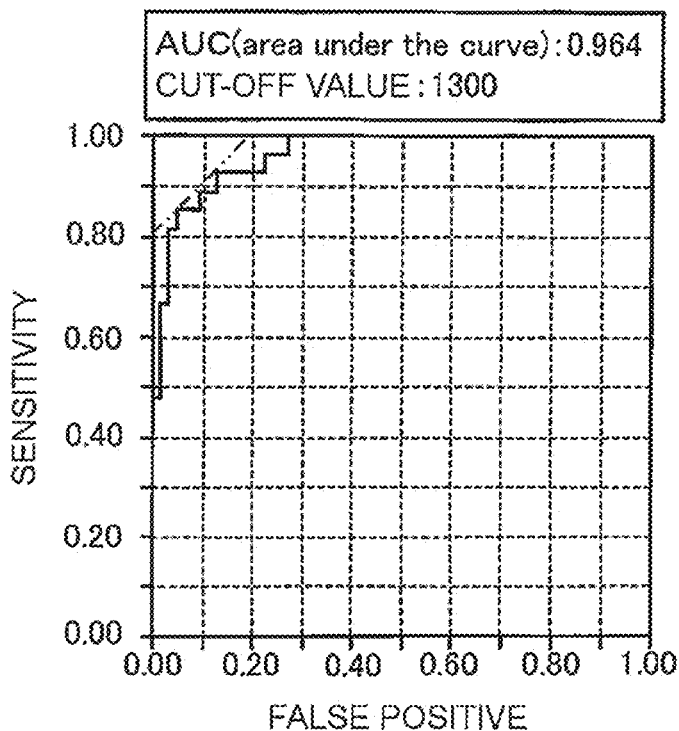
FIG. 23 includes diagrams for illustrating (a) an ROC curve and (b) a sensitivity, a false positive rate, a false negative rate, and a specificity in a case where the second asymmetric index acquired by the scoliosis diagnosis assistance device according to the second embodiment is applied to a diagnosis of whether the Cobb angle represents scoliosis of 25 degrees or more.

FIG. 22 and FIG. 23 are examples of a case in which a subject is diagnosed with scoliosis (diagnosed with scoliosis in a stage that requires equipment) when the Cobb angle indicates 25 degrees or more. Each of FIG. 22 and FIG. 23 indicates a result of applying each of the first asymmetric index and the second asymmetric index to such a diagnosis.

When the first asymmetric index is used to diagnose a subject whose Cobb angle indicates 25 degrees or more with scoliosis, and a cut-off value is set to 163,465 based on the ROC curve as indicated in FIG. 22(a), as indicated in FIG. 22(b), the sensitivity and the specificity are set to 0.926 and 0.873, respectively.

When the second asymmetric index is used to diagnose a subject whose Cobb angle indicates 25 degrees or more with scoliosis, and a cut-off value is set to 1,300 based on the ROC curve as indicated in FIG. 23(a), as indicated in FIG. 23(b), the sensitivity and the specificity are set to 0.852 and 0.952, respectively.

Figure 24:
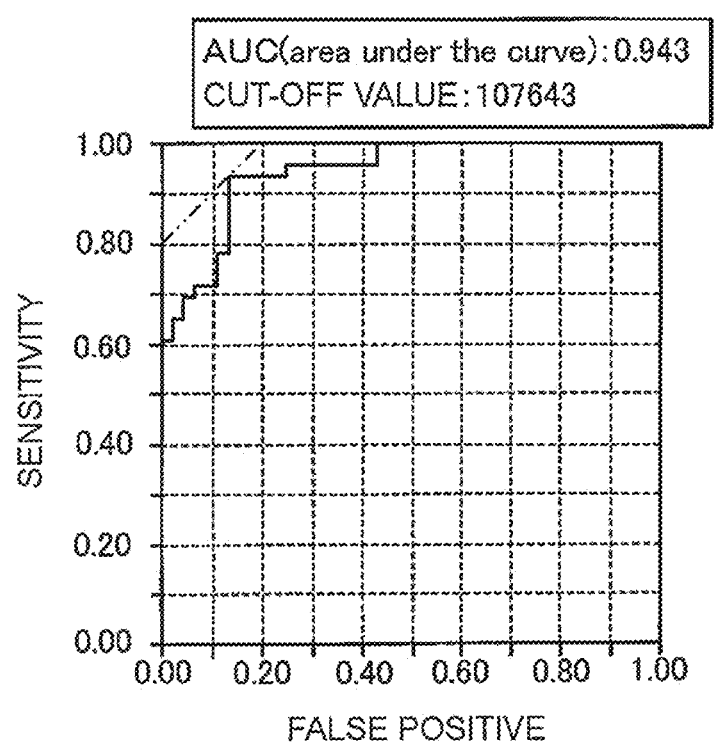
FIG. 24 includes diagrams for illustrating (a) an ROC curve and (b) a sensitivity, a false positive rate, a false negative rate, and a specificity in a case where the first asymmetric index acquired by the scoliosis diagnosis assistance device according to the second embodiment is applied to a diagnosis of whether the Cobb angle represents scoliosis of 15 degrees or more.
Figure 25:
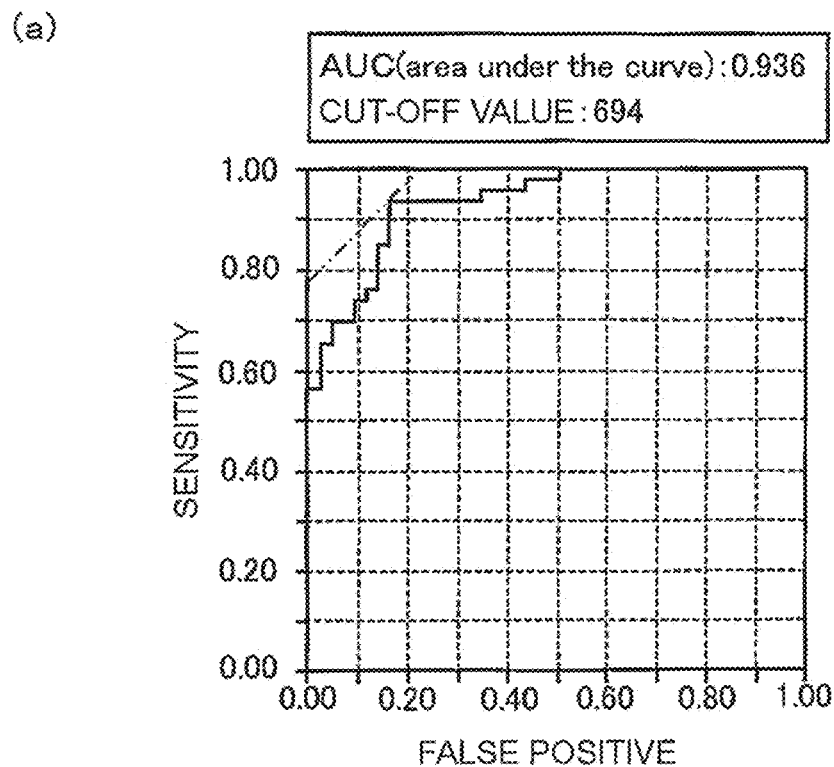
FIG. 25 includes diagrams for illustrating (a) an ROC curve and (b) a sensitivity, a false positive rate, a false negative rate, and a specificity in a case where the second asymmetric index acquired by the scoliosis diagnosis assistance device according to the second embodiment is applied to a diagnosis of whether the Cobb angle represents scoliosis of 15 degrees or more.

FIG. 24 and FIG. 25 are examples of a case in which a subject is diagnosed with scoliosis (diagnosed with scoliosis in a stage that requires equipment) when the Cobb angle indicates 15 degrees or more. Each of FIG. 24 and FIG. 25 indicates a result of applying each of the first asymmetric index and the second asymmetric index to such a diagnosis.

When the first asymmetric index is used to diagnose a subject whose Cobb angle indicates 15 degrees or more with scoliosis, and a cut-off value is set to 107,643 based on the ROC curve as indicated in FIG. 24(a), as indicated in FIG. 24(b), the sensitivity and the specificity are set to 0.935 and 0.864, respectively.

When the second asymmetric index is used to diagnose a subject whose Cobb angle indicates 15 degrees or more with scoliosis, and a cut-off value is set to 694 based on the ROC curve as indicated in FIG. 25(a), as indicated in FIG. 25(b), the sensitivity and the specificity are set to 0.935 and 0.841, respectively.

In general, a likelihood ratio is adopted in order to determine whether the relevant diagnosis method is useful for diagnosis of a disease. The likelihood ratio is obtained by dividing the "probability of a person in the state obtaining the examination result" by the "probability of a person not in the state obtaining the examination result". For example, when the likelihood ratio in a case where the inspection result is positive is defined as a positive likelihood ratio, the positive likelihood is obtained by an expression of "positive likelihood ratio=sensitivity/false positive rate=sensitivity/(1-specificity)". Further, for example, when the likelihood ratio in a case where the inspection result is negative is defined as a negative likelihood ratio, the negative likelihood ratio is obtained by an expression of "negative likelihood ratio=false negative rate/specificity=(1-sensitivity)/specificity".

The positive likelihood ratio becomes more useful as the positive likelihood ratio indicates a larger value, and in general, is said to be useful for a definitive diagnosis when the positive likelihood ratio indicates 10 or more. The negative likelihood ratio becomes more useful for a diagnosis of exclusion as the negative likelihood ratio indicates a smaller value, and in general, is said to be useful for a diagnosis of exclusion when the negative likelihood ratio indicates 0.1 or less.

FIG. 26 is a figure for showing a likelihood ratio in a case where the first and second asymmetric indices are both applied to diagnosis of scoliosis as described above.

As can be seen from FIG. 26, when the first asymmetric index is used to diagnose a subject whose Cobb angle is 25 degrees or more with scoliosis, the negative likelihood ratio indicates 0.1 or less. Thus, the first asymmetric index is considered to be useful for a diagnosis of exclusion when a subject whose Cobb angle is 25 degrees or more is diagnosed with scoliosis.

When the second asymmetric index is used to diagnose a subject whose Cobb angle is 25 degrees or more with scoliosis, the positive likelihood ratio indicates 10 or more. Thus, the second asymmetric index is considered to be useful for a definitive diagnosis when a subject whose Cobb angle is 25 degrees or more is diagnosed with scoliosis.

When the first asymmetric index is used to diagnose a subject whose Cobb angle is 15 degrees or more with scoliosis, the negative likelihood ratio indicates 0.1 or less. Thus, the first asymmetric index is considered to be useful for a diagnosis of exclusion when a subject whose Cobb angle is 15 degrees or more is diagnosed with scoliosis.

When the second asymmetric index is used to diagnose a subject whose Cobb angle is 15 degrees or more with scoliosis, the negative likelihood ratio indicates 0.1 or less. Thus, the second asymmetric index is considered to be useful for a diagnosis of exclusion when a subject whose Cobb angle is 15 degrees or more is diagnosed with scoliosis.

In this manner, each of the first asymmetric index and the second asymmetric index is an index useful for a definitive diagnosis or a diagnosis of exclusion of scoliosis, which is an easily obtained value. Thus, it is possible to detect scoliosis in an early stage by using one of the first asymmetric index and the second asymmetric index. Further, it is possible to detect scoliosis in an early stage more accurately by using both of the first asymmetric index and the second asymmetric index.

In the above, the embodiments of this invention are described. However, this invention is not limited to those embodiments. For example, this invention may be modified as described below, and may include a mode in which the embodiments and the modification examples are partially or entirely combined in a suitable manner or a mode suitably changed from the mode of combination.

Modification Example 1

The deviation distribution acquisition module 105 may identify, as the plurality of corresponding points, a combination of a plurality of points on the back mesh and a plurality of points on the mirror-symmetric mesh that are positioned perpendicular to the respective plurality of points on the back mesh with respect to the coronal plane. Alternatively, the deviation distribution acquisition module 105 may identify, as the plurality of corresponding points, a combination of a plurality of points on the mirror-symmetric mesh and a plurality of points on the back mesh that are positioned perpendicular to the respective plurality of points on the mirror-symmetric mesh with respect to the coronal plane.

That is, the deviation distribution acquisition module 105 in Modification Example 1 is configured to identify, as the plurality of corresponding points, a combination of a plurality of vertices on a mesh being the three-dimensional shape represented by one of the back shape information and the mirror-symmetry information and a plurality of vertices on a mesh being the three-dimensional shape represented by another of the back shape information and the mirror-symmetry information, which are positioned in a direction perpendicular to the respective plurality of points on the mesh being the three-dimensional shape represented by the one of the back shape information and the mirror-symmetry information with respect to a coronal plane.

Also in Modification Example 1, the distribution of deviations for the entire back of the subject can easily be obtained. Therefore, effects similar to those of the embodiments are exhibited.

Modification Example 2

The method of acquiring the mirror-symmetric mesh described in the embodiments is just one example.

For example, the mirror-symmetric mesh may be stored in advance in a mirror-symmetric mesh storage (not shown) constructed by, for example, a flash memory. Then, the second shape information acquisition module 104 may acquire the mirror-symmetric mesh from the mirror-symmetric mesh storage.

Modification Example 3

The first shape information acquisition module 101 may further include a first image extraction device (not shown) for excluding, from the back shape information output from the smoothing module 116, arms of the subject contained in the back shape information. For example, on the basis of the back mesh represented by the back shape information, the first image extraction device may analyze a horizontal cross-section, detect left and right local minimum points on the cross-sectional curve, and extract only the mesh present between those left and right local minimum points as the back mesh.

According to Modification Example 3 of this invention, the back appearance of the subject represented by the scan data and the color image data may not be a posture of the subject folding hands, and standing or bending forward with both arms being extended.

Modification Example 4

The first shape information acquisition module 101 may further include a second image extraction module (not shown) storing in advance a rectangular frame that is defined depending on a normal back. In this case, the second image extraction module may output information in the rectangular frame as the back shape information within the back shape information output from the smoothing module 116.

According to Modification Example 4 of this invention, the back appearance of the subject represented by the scan data and the color image data may not be a posture of the subject folding hands, and standing or bending forward with both arms being extended.

Modification Example 5

The adjustment module 106 may not be included in the scoliosis diagnosis assistance device 100. Alternatively, the adjustment module 106 may include the mesh adjustment module 118 without including the posture adjustment module 117.

With this, the processing of the posture adjustment module 117 and the mesh adjustment module 118 or the processing of the posture adjustment module 117 is not required to be performed, and thus it is possible to speed up the entire processing.

In particular, when the adjustment module 106 is not included, the accuracy of the distribution of deviations becomes lower than a case in which the adjustment module 106 is included, and thus overdetection is considered to occur. Therefore, this modification example is useful for first screening of whether the subject is suffering from scoliosis.

Modification Example 6

In the second embodiment, a description has been given of an example of adopting the height of the subject as the value indicating the size of the body of the subject, and dividing the first asymmetric index by the height of the subject to acquire the second asymmetric index. However, the second asymmetric index is only required to be obtained by standardizing the first asymmetric index by the size of the body of the subject, and the value indicating the size of the body of the subject is not limited to the height. For example, the area of the back region of the subject or the shoulder width of the subject may be adopted as the value indicating the size of the body of the subject. The area or shoulder width of the back region can be obtained from the color image data acquired by the scoliosis diagnosis assistance device 200 without additionally being acquired as in the case of the height. Therefore, it is possible to obtain the second asymmetric index more easily.

INDUSTRIAL APPLICABILITY

This invention is useful for, for example, an apparatus for assisting in diagnosis by a doctor of whether a subject is suffering from scoliosis or whether a subject requires equipment.

EXPLANATION OF REFERENCE SIGNS

100, 200 scoliosis diagnosis assistance device
101, 201 first shape information acquisition module
102 principal axis acquisition module
103 sagittal plane acquisition module
104 second shape information acquisition module
105 deviation distribution acquisition module
106 adjustment module
107 deviation acquisition module
108 asymmetric data storage
109, 209 asymmetric index acquisition module
110, 210 display controller
111, 211 display
112 subject data acquisition module
113, 213 region setting module
114 cutting out module
115 mesh generation module
116 smoothing module
117 posture adjustment module
118 mesh adjustment module
119 first independent point identification module
120 second independent point identification module
121 independent point adjustment module

The invention claimed is:

1. A scoliosis diagnosis assistance device, comprising:
   at least one memory configured to store program instructions; and
   at least one processor, configured to execute the program instructions which configure the at least one processor as:
      a first shape information acquisition module configured to acquire back shape information representing a three-dimensional shape of a back of a subject based on a scan data representing a three-dimensional shape including the back appearance of the subject with a plurality of points, generated by a device which can generate the scan data;
      a second shape information acquisition module configured to acquire mirror-symmetry information representing a three-dimensional shape having a mirror-symmetry relationship with the three-dimensional shape of the back of the subject with respect to a sagittal plane of the three-dimensional shape, based on the back shape information;
      a diagnosis assistance information module configured to acquire a distribution of deviations between the three-dimensional shape represented by the acquired back shape information and the three-dimensional shape represented by the acquired mirror-symmetry information; and
      an output controller configured to cause an output device to output diagnosis assistance information for assisting in diagnosis of scoliosis for the subject, the diagnosis assistance information being information acquired based on the acquired distribution of deviations.

2. A scoliosis diagnosis assistance device according to claim 1, further comprising an asymmetric index acquisition module configured to acquire, as the diagnosis assistance information, a first asymmetric index indicating a degree to which the three-dimensional shape of the back is asymmetric based on the acquired distribution of deviations and on an entire area of the three-dimensional shape represented by the back shape information.

3. A scoliosis diagnosis assistance device according to claim 2, wherein the asymmetric index acquisition module is configured to acquire, as the diagnosis assistance information together with the first asymmetric index or in place of the first asymmetric index, a second asymmetric index by dividing the acquired first asymmetric index by a value indicating a size of a body of the subject.

4. A scoliosis diagnosis assistance device according to claim 1, wherein the output controller is configured to cause the output device to output the acquired distribution of deviations as the diagnosis assistance information.

5. A scoliosis diagnosis assistance device according to claim 4, wherein the output controller is configured to cause the output device to display the acquired distribution of deviations as the diagnosis assistance information by a color map image, which is an image obtained by coloring the three-dimensional shape of the back of the subject with a color determined in advance depending on each of the deviations.

6. A scoliosis diagnosis assistance device according to a claim 1, wherein the diagnosis assistance information module is configured to identify a plurality of corresponding points between the three-dimensional shape represented by the acquired back shape information and the three-dimensional shape represented by the acquired mirror-symmetry information, and acquire respective distances between the plurality of corresponding points as the distribution of deviations.

7. A scoliosis diagnosis assistance device according to claim 6, wherein the diagnosis assistance information module is configured to identify, as the plurality of corresponding points, a combination of points which are positioned closest to each other between a plurality of points on the three-dimensional shape represented by one of the back shape information and the mirror-symmetry information and a plurality of points on the three-dimensional shape represented by another of the back shape information and the mirror-symmetry information.

8. A scoliosis diagnosis assistance device according to claim 6, wherein the diagnosis assistance information module is configured to identify, as the plurality of corresponding points, a combination of points which are positioned in a direction perpendicular to a coronal plane each other between a plurality of points on the three-dimensional shape represented by one of the back shape information and the mirror-symmetry information and a plurality of points on the three-dimensional shape represented by another of the back shape information and the mirror-symmetry information.

9. A scoliosis diagnosis assistance device according to claim 1, further comprising a sagittal plane acquisition module configured to acquire a sagittal plane of the three-dimensional shape represented by the acquired back shape information,
   wherein the second shape information acquisition module is configured to acquire the mirror-symmetry information based on the three-dimensional shape represented by the acquired back shape information and on the acquired sagittal plane.

10. A scoliosis diagnosis assistance device according to claim 9, further comprising a principal axis acquisition module configured to subject the three-dimensional shape represented by the acquired back shape information to principal component analysis, to thereby acquire two principal axes, which corresponds to an up-down direction and a front-back direction of the subject, in a space having a group of points on the three-dimensional shape represented by the acquired back shape information,
   wherein the sagittal plane acquisition module is configured to acquire the sagittal plane of the three-dimensional shape represented by the acquired back shape information based on the acquired two principal axes.

11. A scoliosis diagnosis assistance device according to claim 1, wherein the diagnosis assistance information module includes
   an adjustment module configured to adjust a positional relationship between the three-dimensional shape represented by the acquired back shape information and the three-dimensional shape represented by the acquired mirror-symmetry information; and
   a deviation acquisition module configured to acquire a distribution of deviations of an entire three-dimensional shape represented by the back shape information, for which a positional relationship with the three-dimensional shape represented by the mirror-symmetry information has been adjusted, from the three-dimensional shape represented by the mirror-symmetry information.

12. A scoliosis diagnosis assistance device according to claim 1, wherein the first shape information acquisition module includes
   a subject data acquisition module configured to acquire scan data representing a plurality of points on a three-dimensional shape of a back appearance of the subject and color image data representing a color image of the back appearance of the subject;

a region setting module configured to compare the acquired color image data with a hue threshold value determined in advance, to thereby extract a back region corresponding to the back of the subject, and set a region identified from the extracted back region with a predetermined method as a region of interest;

a cutting out module configured to cut out, from the scan data, a plurality of points in a region corresponding to the set region of interest; and a mesh generation module configured to generate, as the back shape information, information representing the three-dimensional shape of the back of the subject with a mesh, based on the plurality of cut-out points.

13. A scoliosis diagnosis assistance method, comprising:

acquiring back shape information representing a three-dimensional shape of a back of a subject based on a scan data representing a three-dimensional shape including the back appearance of the subject with a plurality of points, generated by a device which can generate the scan data;

acquiring mirror-symmetry information representing a three-dimensional shape having a mirror-symmetry relationship with the three-dimensional shape of the back of the subject with respect to a sagittal plane of the three-dimensional shape, based on the back shape information;

acquiring a distribution of deviations of an entire three-dimensional shape represented by the acquired back shape information from the three-dimensional shape represented by the acquired mirror-symmetry information; and causing an output device to output diagnosis assistance information for assisting in diagnosis of scoliosis for the subject, the diagnosis assistance information being information acquired based on the acquired distribution of deviations.

14. A non-transitory computer readable recording medium storing a program for causing a computer to function as:

a first shape information acquisition module configured to acquire back shape information representing a three-dimensional shape of a back of a subject based on a scan data representing a three-dimensional shape including the back appearance of the subject with a plurality of points, generated by a device which can generate the scan data;

a second shape information acquisition module configured to acquire mirror-symmetry information representing a three-dimensional shape having a mirror-symmetry relationship with the three-dimensional shape of the back of the subject with respect to a sagittal plane of the three- dimensional shape, based on the back shape information;

a diagnosis assistance information module configured to acquire a distribution of deviations of an entire three-dimensional shape represented by the acquired back shape information from the three-dimensional shape represented by the acquired mirror-symmetry information; and an output controller configured to cause an output device to output diagnosis assistance information for assisting in diagnosis of scoliosis for the subject, the diagnosis assistance information being information acquired based on the acquired distribution of deviations.

* * * * *